US006207412B1

(12) United States Patent
Weng et al.

(10) Patent No.: US 6,207,412 B1
(45) Date of Patent: Mar. 27, 2001

(54) IDENTIFICATION OF A G PROTEIN-COUPLED RECEPTOR TRANSCRIPTIONALLY REGULATED BY PROTEIN TYROSINE KINASE SIGNALING IN HEMATOPOIETIC CELLS

(75) Inventors: Zhigang Weng, Los Angeles; Owen N. Witte, Sherman Oaks, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/969,815

(22) Filed: Nov. 13, 1997

(51) Int. Cl.⁷ ............................. C12N 15/12; C12N 15/63
(52) U.S. Cl. ..................... 435/69.1; 435/320.1; 435/325; 435/252.3; 435/172.3; 536/24.31; 536/23.1
(58) Field of Search ................................. 536/23.5, 23.1, 536/24.31; 435/69.1, 172.3, 252.3, 320.1, 325; 530/350, 300

(56) References Cited

PUBLICATIONS

Libert, F et al. Selective Amplification and Cloning of Four New Members of the G Protein–Coupled Receptor Family Science, vol. 244 pp. 569–572, 1989.*
Bouvier, M et al. Dynamic Palmitoylation of G–Protein–Coupled Receptors in Eukaryotic Cells. Methods in Enzymology, Academic Press, pp. 300–314, 1995.*
Afar, et al., "Differential Complementation of Bcr–Abl Point Mutants with c–Myc", *Science*, 164 :424–426 (Apr. 15, 1994).
Afar, et al., "Signaling by ABL oncogenes through cyclin D1", *Proc. Natl. Acad. Sci. USA*, 92 :9540–9544 (Oct. 1995).
Alkhatib, et al., "CC CKR5: A Rantes, MIP–1β Receptor as a Fusion Cofactor for Macrophage–Tropic HIV–1", *Science*, 272 :19551958 (Jun. 28, 1996).
Arvanitakis, et al., "Human herpesvirus KSHV encodes a constitutively active G–protein–coupled receptor linked to cell proliferation", *Nature*, 385 :347–350 (Jan. 23, 1997).
Braun, et al., "Identification of Target Genes for the Ewing's Sarcoma EWS/FLI Fusion Protein by Representational Difference Analysis", *Molecular and Cellular Biology*, 15(8) :4623–4630 (Aug. 1995).
Choe, et al., "The β–Chemokine Receptos CCR3 and CCR5 Facilitate Infection by Primary HIV–1 Isolates", *Cell*, 85 :1135–1148 (Jun. 28, 1996).
Davis, R.J., "Transcriptional Regulation by MAP Kinases", *Molecular Reproduction and Development*, 42 :459–467 (1995).
Deng, et al.,"Identification of a major co–receptor for primary isolates of HIV–1", *Nature*, 381 :661–666 (Jun. 20, 1996).
Choi, et al., "Identification of a Putative G Protein–Coupled Receptor Induced during Activation–Induced Apoptosis of T Cells", *Cellular Immunology*, 168 :78–84 (1996).

Doranz, et al., "A Dual–Tropic Primary HIV–1 Isolate That Uses Fusin and the β–Chemokine Receptors CKR–5, CKR–3, and CKR–2b as Fusion Cofactors", *Cell*, 85 :1148–1158 (Jun. 28, 1996).
Dragic, et al., "HIV–1 entry in to CD4⁺ cells is mediated by the chemokine receptor CC–CRK–5", *Nature*, 381 :667–673 (Jun. 20, 1996).
Feng, et al., "HIV–1 Entry Cofactor: Functional cDNA Cloning of a Seven–Transmembrane, G Protein–Coupled Receptor", *Science*, 272 :872–877 (May 10, 1996).
Förster, et al., "A Putative Chemokine Receptor, BLR1, Directs B Cell Migration to Defined Lymphoid Organs and Specific Anatomic Compartments of the Spleen", *Cell*, 87 :1037–1047 (Dec. 13, 1996).
Fu, M.L.X., "Characterization of anti–heart M2 muscarinic receptor antibodies—a combined clinical and experimentally study", *Molecular and Cellular Biochemistry*, 163/164 :343–347 (1996).
Goga, et al., "Alternative Signals to RAS for Hematopoietic Transformation by the BCR–ABL Oncogene", *Cell*, 82 :981–988 (Sep. 22, 1995).
Hubank, et al., "Identifying differences in mRNA expression by representational difference analysis of cDNA", *Nucleic Acids Research*, 22(25) :5640–5648 (1994).
Koshiba, et al., "Transient up–regulation of P2Y₂ nucleotide receptor mRNA expression is an immediate early gene response in activated thymocytes", *Proc. Natl. Acad. Sci. USA*, 94 :831–836 (Feb. 1997).
Kurzrock, et al., "The Molecular Genetics of Philadelphia Chromosome—Positive Leukemias", *The New England Journal of Medicine*, 319(15) :990–998 (Oct. 13, 1988).
Lugo, et al., "The BCR0ABL Oncogene Transform Rat–1 Cells and Cooperates with v–myc", *Molecular and Cellular Biology*, 9(3) :1263–1270 (Mar. 1989).
McLaughlin, et al., "Alternative Forms of the BCR–ARL Oncogene Have Quantitatively Different Potencies for Stimulation of Immature Lymphoid Cells", *Molecular and Cellular Biology*, 9(5) :1866–1874 (May 1989).
Muller, et al., "BCR Firs Exon Sequences Specifically Activate the BCR/ABL Tyrosine Kinase Oncogene of Philadelphia Chromosome–Positive Human Leukemias", *Molecular and Cellular Biology*, 11(4) :1785–1792 (Apr. 1991).
Murphy, P.M., "The Molecular Biology of Leukocyte Chemoattractant Receptors", *Annu. Rev. Immunol.*, 12 :593–633 (1994).

(List continued on next page.)

Primary Examiner—Yvonne Eyler
Assistant Examiner—Nirmal S. Basi
(74) Attorney, Agent, or Firm—Gates & Cooper LLP

(57) ABSTRACT

A G protein-coupled receptor (GPCR) which is activated by oncogenes. The receptor is found predominantly in hematopoietic cells and tissues and functions as a tumor suppressor gene and induces cell cycle arrest. This receptor may play an important role in regulating the proliferation and differentiation of hematopoietic cells. Regulation of receptor activity has several therapeutic applications.

6 Claims, 3 Drawing Sheets

OTHER PUBLICATIONS

Pear, et al., "Production of high–titer helper–free retroviruses by transient transfection", *Proc. Natl. Acad. Sci. USA*, 90 :8392–8396 (Sep. 1993).

Pendergast, et al., "BCR–ABL1–Induced Oncogenesis Is Mediate by Direct Interaction with the SH2 Domain of the GRB–2 Adaptor Protein", *Cell*, 75 :175–185 (Oct. 8, 1993).

Schneider, et al., "Genes Specifically Expressed at Growth Arrest of Mammalian Cells", *Cell*, 54 :787–793 (Sep. 9, 1988).

Strader, et al., "The family of G–protein–coupled receptors", *The FASEB Journal*, 9 :745–754 (Jun. 1995).

Strader, et al., "Structure and Function of G Protein–Coupled Receptors", *Annu. Rev. Biochem.*, 63 :101–132 (1994).

Tsukada, et al., "Deficient Expression of a B Cell Cytoplasmic Tyrosine Kinase in Human X–Linked Agammaglobulinemia", *Cell*, 72 :279–290 (Jan. 29, 1993).

Lisitsyn, et al., "Cloning the Differences Between Two Complex Genomes", *Science*, 259 :946–951 (Feb. 12, 1993).

* cited by examiner

Alignment of Mouse and Human GPCRs

```
  1  MRSEPTNAAGNTTLGVTSVLQSTSVPSSETCHVSYEESRVVLVVVYSAVC   50  Mouse
     |     . .|.:..|..:.|      :||:||||:||||||||||
  4  MLLKNGYNGNATPVTTTAPWASLGLSAKTCNNVSFEESRIVLVVVYSAVC   53  Human 51  LLGLPANCLTAWLTLLQVLQRNVLAVYLFCLSLCELLYISTVPLWIIYIQ  100  Mouse
     ||:|||||||||.||||||  ||||||:||.||||||..:|:|||:|||.
 54  TLGVPANCLTAWLALLQVLQGNVALVYLLCLALCELLYTGTLPLWVIYIR  103  Human 101  NQHKWNLGPQACKVTAYIFFCNIYISILLLCCISCDRYMAVVYALESRGH  150  Mouse
     |||:|.||  |||||||||||||:|||:||||||||||:::|||||||||:
104  NQHRWTLGLLACKVTAYIFFCNIYVSILFLCCISCDRFVAVVYALESRGR  153  Human 151  RHQRTAVTISACVILLVGLVNYPVFDMKVEKSFCFEPLRMNSKIAGYHYL  200  Mouse
     |:.|||: ||||:::|||:|:||||:  .:|. ||: |.|:|:||||.|
154  RRRRTAILISACIFILVGIVHYPVFQTE.DKETCFDMLQMDSRIAGYYYA  202  Human 201  RFTFGFAIPLGILAFTNHQIFRSIKLSDSLSAAQKNKVKRSAIAVVTIFL  250  Mouse
     |||.|||||||:|:|||||.||||||  :|||||||.|||:||||||.|||
203  RFTVGFAIPLSIIAFTNHRIFRSIKQSMGLSAAQKAKVKHSAIAVVVIFL  252  Human 251  VCFAPYHVVLLVKAASFSFYQGDMDAVCAFESRLYTVSMVFLCLSTVNSV  300  Mouse
     |||||||:||||||.||:|.||.:|:::|.||||.|:|||||||||||:|
253  VCFAPYHLVLLVKAAAFSYYRGDRNAMCGLEERLYTASVVFLCLSTVNGV  302  Human 301  ADPIIYVLGTDHSRQEVSRIHTGWKKWSTKTYV...TCSKDSEETHLPTE  347  Mouse
     ||||||||:||||||||||||:||.||  ||  |    | |:|.|| :|..
303  ADPIIYVLATDHSRQEVSRIHKGWKEWSMKTDVTRLTHSRDTEELQSPVA  352  Human 348  LSNTYTFPNPAHPPGSQPAKLGLLCSPERLPEELC  382  Mouse
     |.:|||...|.|||||.        |.:||||||
353  LADHYTFSRPVHPPGSP.......CPAKRLIEESC  380  Human
```

FIG. 3

IDENTIFICATION OF A G PROTEIN-COUPLED RECEPTOR TRANSCRIPTIONALLY REGULATED BY PROTEIN TYROSINE KINASE SIGNALING IN HEMATOPOIETIC CELLS

GOVERNMENT SUPPORT

This invention was made with Government support under NIH grant number CA 53867. The Government has certain rights in the invention.

FIELD OF THE INVENTION

The present invention relates to a G protein-coupled receptor whose expression is regulated in hematopoietic cells upon activation and functions as a tumor suppressor gene.

BACKGROUND OF THE INVENTION

The family of G protein-coupled receptors (GPCRs) has at least 250 members (Strader et al. *FASEB J.,* 9:745–754, 1995; Strader et al. *Annu. Rev. Biochem.,* 63:101–32, 1994). It has been estimated that one percent of human genes may encode GPCRs. GPCRs bind to a wide-variety of ligands ranging from photons, small biogenic amines (i.e., epinephrine and histamine), peptides (i.e., IL-8), to large glycoprotein hormones (i.e., parathyroid hormone). Upon ligand binding, GPCRs regulate intracellular signaling pathways by activating guanine nucleotide-binding proteins (G proteins). GPCRs play important roles in diverse cellular processes including cell proliferation and differentiation, leukocyte migration in response to inflammation, and cellular response to light, odorants, neurotransmitters and hormones (Strader et al., supra.).

Interestingly, GPCRs have functional homologues in human cytomegalovirus and herpesvirus, suggesting that GPCRs may have been acquired during evolution for viral pathogenesis (Strader et al., *FASEB J.,* 9:745–754, 1995; Arvanitakis et al. *Nature,* 385:347–350, 1997; Murphy, *Annu. Rev. Immunol.* 12:593–633, 1994).

The importance of G protein-coupled receptors is further highlighted by the recent discoveries that its family members, chemokine receptors CXCR4/Fusin and CCR5, are co-receptors for T cell-tropic and macrophage-tropic HIV virus strains respectively (Alkhatib et al., *Science,* 272:1955, 1996; Choe et al., *Cell,* 85:1135, 1996; Deng et al., *Nature,* 381:661, 1996; Doranz et al., *Cell,* 85:1149, 1996; Dragic et al., *Nature,* 381:667 (1996); Feng et al., *Science* 272:872, 1996). It is conceivable that blocking these receptors may prevent infection by the human immunodeficiency (HIV) virus.

BCR-ABL is a chimeric tyrosine kinase oncogene generated by a reciprocal chromosomal translocation t(9;22). This chimeric oncogene found in $Ph^1$-positive stem cells is associated with the pathogenesis of chronic myelogenous leukemia and acute lymphocytic leukemia. Mutational analysis has defined critical domains within BCR-ABL important for its functions. In particular, inactivation of the SH2 domain greatly reduced the malignant and leukemogenesis potential of BCR-ABL in vivo.

SUMMARY OF THE INVENTION

One embodiment of the present invention is an isolated polynucleotide having the nucleotide sequence shown in SEQ ID NO: 1 or 3.

The present invention also provides an isolated polynucleotide encoding a G protein-coupled receptor (GPCR) regulated by a protein tyrosine kinase, wherein said polynucleotide is capable of hybridizing to a polynucleotide having the sequence shown in SEQ ID NO: 1 at 65° C. in 2×SSC, 0.1% SDS.

Another embodiment of the invention is an isolated, recombinant protein tyrosine kinase-regulated GPCR having the amino acid sequence shown in SEQ ID NO: 2 or 4. Preferably, the protein having the amino acid sequence shown in the SEQ ID NO: 2 is obtained by expression of a polynucleotide having the sequence shown in SEQ ID NO: 1. Advantageously, the protein having the amino acid sequence shown in the SEQ ID NO: 4 is obtained by expression of a polynucleotide having the sequence shown in SEQ ID NO: 3.

The present invention also provides an isolated GPCR encoded by a polynucleotide having the sequence shown in SEQ ID NO: 1 at 65° C. in 2×SSC, 0.1% SDS.

Another embodiment of the invention is isolated antibodies to the GPCR described above. Preferably, the antibodies are polyclonal. Alternatively, the antibodies are monoclonal.

Another embodiment of the invention is a method of identifying a compound which activates the protein tyrosine kinase-regulated GPCR, comprising the steps of contacting the GPCR with a test compound; determining whether the compound binds to the GPCR; and testing compounds which bind to said GPCR in a receptor activity assay, whereby stimulation of receptor activity indicates that the compound is an activator of the GPCR. Preferably, the GPCR is expressed on the cell surface. Advantageously, the receptor activity assay is fibroblast transformation, bone marrow transformation, cell cycle analysis, in vivo tumor formation or in vivo leukemogenesis.

The present invention also provides a method of identifying a compound which inhibits the protein tyrosine kinase-regulated GPCR, comprising the steps of: contacting the GPCR with a test compound; determining whether the compound binds to the GPCR; and testing compounds which bind to the GPCR in a receptor activity assay, whereby inhibition of receptor activity indicates that the compound is an inhibitor of the GPCR. Preferably, the GPCR is expressed on the cell surface. Advantageously, the receptor activity assay is fibroblast transformation, bone marrow transformation, cell cycle analysis, in vivo tumor formation or in vivo leukemogenesis.

Another embodiment of the invention is a method of identifying a compound which activates the protein tyrosine kinase-regulated GPCR, comprising the steps of: contacting the GPCR with a test compound; determining whether the compound binds to the GPCR; and testing compounds which bind to the GPCR in a receptor activity assay, whereby activation of receptor activity indicates that the compound is an inhibitor of the GPCR. Preferably, the GPCR is expressed on the cell surface. Advantageously, the receptor activity assay is fibroblast transformation, bone marrow transformation, cell cycle analysis, in vivo tumor formation or in vivo leukemogenesis.

The tester DNA is hybridized to an excess of driver DNA. DNA fragments from differentially-expressed genes will form homodimers with the new adapters at both ends and can be exponentially amplified by PCR. Fragments present in both driver efficiently amplified. The process is repeated 3–4 times and differentially amplified DNA fragments are subcloned for further analysis.

Figure 2:
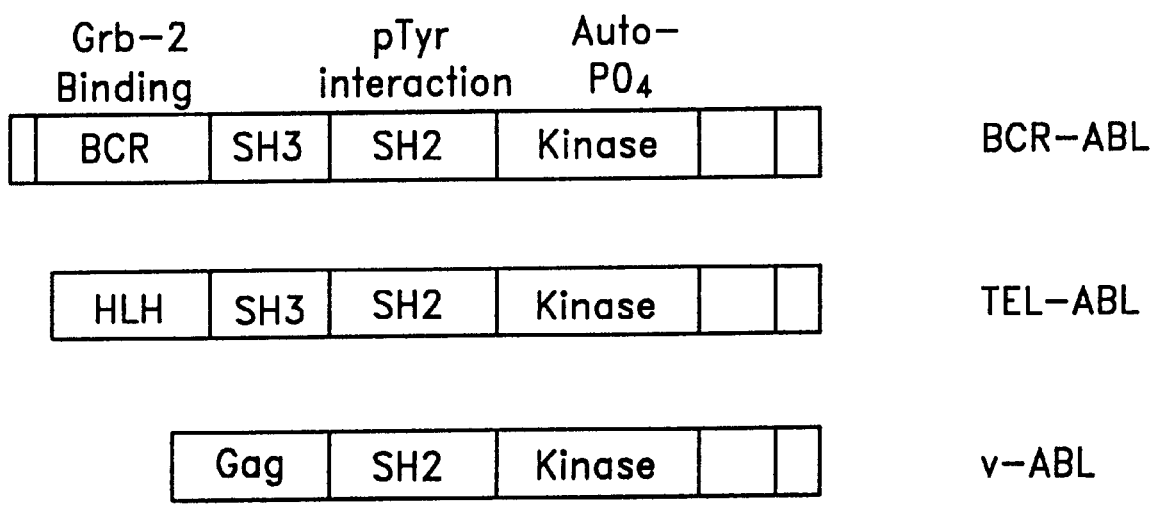

FIG. 2 is a schematic diagram showing the various domains of BCR-ABL, TEL-ABL and v-ABL. SH3=src homology region 3; SH2=src homology region 2; pTyr= phosphotyrosine; Auto-$PO_4$=autophosphorylation site; Grb-2=adaptor protein which couples BCR-ABL to Ras; HLH= helix-loop helix domain involved in oligomerization of the protein and activation of Abl kinase activity.

FIG. 3 shows a sequence alignment of the murine (SEQ ID NO:2) and human (SEQ ID NO:4) GPCRs. The human and murine GPCRs share approximately 70% identity at the amino acid level.

DETAILED DESCRIPTION OF THE INVENTION

Figure 1:
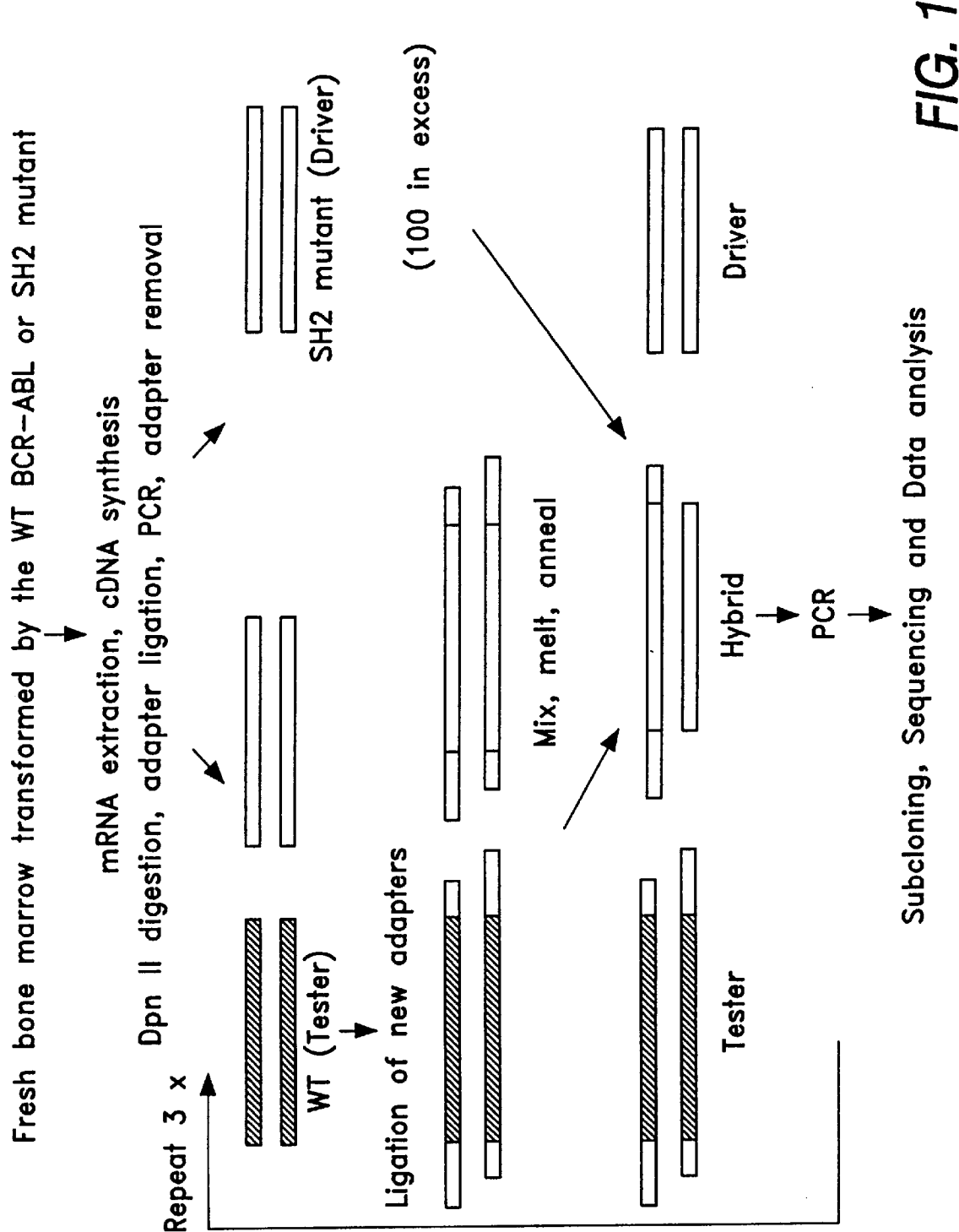
FIG. 1 is a schematic diagram depicting the isolation of differentially-expressed genes by representational difference analysis (RDA). After mRNA isolation and cDNA synthesis, tester and driver cDNAs are digested with a restriction enzyme (RE) and ligated with adapters. After PCR amplification, the adaptors are removed by RE digestion and new adaptors are ligated to the tester DNA fragments only.

The present invention describes the identification and sequencing of a novel G protein-coupled receptor (GPCR) that is transcriptionally upregulated by protein tyrosine kinase signaling and during lymphocyte activation. The GPCR functions as a tumor suppressor gene, induces cell cycle arrest during mitosis and is found on human chromosome 14q32.3, a region frequently found altered in human cancers. This GPCR was identified while studying cellular genes that can be regulated by BCR-ABL, a chimeric tyrosine kinase oncogene associated with the pathogenesis of chronic myelogenous leukemia (CML) and acute lymphocytic leukemia (ALL) (Kurzrock, N. Engl. J Med. 319: 990–998, 1988). Using a PCR-based differential screening technique (representational difference analysis or RDA) (Lisitsyn et al. Science 259:946–951, 1993; Hubank et al., Nucl. Acids Res. 22:5640–5648, 1994; FIG. 1), genes expressed in murine bone marrow cells transformed by the wild type (WT) BCR-ABL were compared to those expressed when a transformation-defective mutant variant carrying a mutation in the SH2 domain of BCR-ABL was used to infect these cells. One of these differentially expressed murine genes (N2A) was predominantly expressed in hematopoietic tissues such as spleen and thymus. The cDNA and deduced amino acid sequences of the murine GPCR are shown in SEQ ID NO: 1 and SEQ ID NO: 2, respectively. The human homologue of the mouse protein was then isolated using the murine cDNA as a probe. The corresponding human cDNA and deduced amino acid sequences are shown in SEQ ID NO: 3 and SEQ ID NO: 4, respectively. The GPCR protein sequence of the invention has the sequence shown in SEQ ID NOS; 2 and 4, or sequence variations thereof which do not substantially compromise the ability of these genes to be regulated by protein tyrosine kinases or sequence variations thereof which do not substantially compromise the functional activities of these proteins. It will be appreciated that GPCR proteins containing one or more amino acid replacements in various positions of the sequences shown in SEQ ID NOS: 2 and 4 are also within the scope of the invention.

Many amino acid substitutions can be made to the native sequence without compromising its functional activity. Variations of these protein sequences contemplated for use in the present invention include minor insertions, deletions and substitutions. For example, conservative amino acid replacements are contemplated. Such replacements are, for example, those that take place within a family of amino acids that are related in the chemical nature of their side chains. The families of amino acids include the basic amino acids (lysine, arginine, histidine); the acidic amino acids (aspartic acid, glutamic acid); the non-polar amino acids (alanine, valine, leucine, isoleucine, proline, phenylalanine, methionine, tryptophan); and the uncharged polar amino acids (glycine, asparagine, glutamine, cysteine, serine, threonine, tyrosine) and the aromatic amino acids (phenylalanine, tryptophan, tyrosine). In particular, it is generally accepted that conservative amino acid replacements consisting of an isolated replacement of a leucine with an isoleucine or valine, or an aspartic acid with a glutamic acid, or a threonine with a serine, or a similar conservative replacement of an amino acid with a structurally related amino acid, in an area outside of the polypeptide's active site, will not have a major effect on the properties of the polypeptide.

The murine protein was determined to be a member of the GPCR superfamily by its homology to other GPCRs, including the mouse TDAG8 protein and the P2Y purinoceptor, using sequence alignment programs. The human GPCR homologue was isolated by screening a human spleen cDNA library under high stringency conditions (2×SSC, 0.1% SDS, 65° C.). The murine and human GPCRs share approximately seventy percent identity at the amino acid level (FIG. 3). Any DNA molecule capable of hybridizing the DNA sequence shown in SEQ ID NO: 1 under these conditions or lower stringency conditions, as well as the protein encoded by such a DNA molecule, is within the scope of the invention.

Northern analysis of various murine tissue samples detected two GPCR transcripts of about 3 kb and 5 kb in spleen, thymus, lung and heart, but not in normal bone marrow, brain, liver, skeletal muscle or kidney. Northern analysis of human tissues showed that the human GPCR is exclusively expressed in spleen and peripheral leukocytes, but not in heart, brain, placenta, lung, liver, skeletal muscle, kidney, pancreas, thymus, prostate, testis, ovary, small intestine and the mucosal lining of the colon. This further suggests a role of this gene in hematopoiesis. The human GPCR is transcriptionally activated in B cells upon activation by either phorbol 12-myristate 13-acetate (PMA) plus ionomycin or anti-IgM antibodies. The activation of GPCR transcription was also observed in B cells upon irradiation with x-rays or activation by the CD40 ligand. The human GPCR transcript is also present in the ALL-1 and K-562 leukemia cell lines.

The GPCR was transcriptionally activated by BCR-ABL and v-Abl, a protein tyrosine kinase oncogene found in Abelson Murine Leukemia Virus. To our knowledge, this is the first demonstration that a GPCR can be transcriptionally regulated by a protein tyrosine kinase. Interestingly, a mutant form of BCR-ABL (carrying a mutation in the SH2 domain) that lacks oncogenic potential failed to transcriptionally activate the GPCR. In addition, Cyclin D1, an important cell cycle regulator (Afar et al., Proc. Natl. Acad. Sci. U.S.A. 92:9540–9544, 1995) that can complement the BCR-ABL mutant for transformation, restored the expression of the GPCR. These data suggest that this GPCR may also be a marker for transformation by BCR-ABL and other tyrosine kinase signaling pathways.

FIG. 2 shows the domains of BCR-ABL, TEL-ABL (an oncogenic fusion protein associated with leukemia) and v-ABL. TEL-ABL, Grb-2 (an adaptor protein which couples BCR-ABL to Ras) mutant and autophosphorylation mutant did not activate the GPCR. The GPCR receptor was also transcriptionally activated by v-Mos, a serine kinase oncogene that activates MAP kinase (Davis, *Mol. Reprod. Dev.* 42:459–67, 1995). Since v-Mos, BCR-ABL and v-ABL all activate MAP kinases (Davis, supra.), the GPCR may be directly regulated by MAP kinase signaling pathways. Therefore, it is contemplated that the GPCR may also be activated by a wide-variety of protein kinases as well as their regulators and effectors during cell growth and differentiation such as Ras, Myc, Fos, Jun and BTK.

The GPCR is expressed in spleen and thymus, but not in normal bone marrow cells, suggesting that it may play an important role in mid- and late stages of T and B cell development. During development, self-reactive immature thymocytes are clonally deleted in the thymus, a phenomenon which establishes T cell tolerance (negative selection). It has been shown that the deletion of self-reactive immature T cells in the thymus is mediated by apoptosis upon T cell receptor engagement. TDAG8, a GPCR family member, is induced in T cells during apoptosis upon T cell receptor activation (Choi et al., *Cell. Immunol.*, 168:78–84, 1996). This suggests that TDAG8 may play a role in negative selection of T cells. Since the GPCRs that we isolated share about 30% homology with TDAG8, it is conceivable that the GPCRs may also play a role in negative selection of T cells. Sequence analysis of the GPCR with its family members reveal that they also share significant homology with the P2Y receptor, a GPCR for ATP. It has been shown recently that P2Y receptor is transcriptionally upregulated during T cell activation (Koshiba et al., *Proc. Natl. Acad. Sci. U.S.A.*, 94:831–836, 1997).

The GPCRs may play a role in directing migration of lymphocytes into specific anatomical compartments of spleen and thymus for maturation. Previous studies on a hematopoietic-specific GPCR, BLR1, suggest that BLR1 plays an important role for directing migration of lymphocytes into splenic follicles as well as migration of activated B cells into B cell-follicles of the spleen, a prerequisite for the development of an antigen-specific immune response (Forster et al., *Cell*, 87:1037–1047, 1996). Expression of GPCRs in hematopoietic-specific tissues suggest that it may also play similar roles in directing migration of lymphocytes into lymphoid organs for their maturation.

The human and murine GPCRs share about 70% identity at the amino acid level based on the translation of their complete cDNA sequences (see FIG. 3). Both the mouse and human GPCR cDNA clones can be used for in situ analysis to examine whether the expression of the receptor is restricted to certain anatomical regions of the spleen and thymus. The mouse and human genomic clones encoding the full length GPCRs were also isolated. The mouse genomic clone has been used for constructing a targeting vector to knock-out the GPCR in mice by homologous recombination. The GPCR –/– mice will allow further evaluation of the physiological functions of this receptor. The GPCR –/– mice will also allow determination of whether in vivo leukemogenesis is dependent on the GPCR. The mouse and human genomic clones may contain the distal and proximal promoters of the GPCRs that will allow the analysis of the transcriptional regulation of hematopoietic-specific genes. Both the mouse and human genomic clones can also be used for cytogenetic mapping to examine whether the GPCRs are linked to any known genetic diseases.

Rabbit antisera was prepared which was reactive with either the N-terminal portion or the C-terminal portion of the receptor as confirmed by ELISA. Two rabbits were injected with a 13 amino-acid peptide corresponding to the cytoplasmic tail of the receptor. Another two rabbits were injected with GST-GPCR-N, a glutathione-S-transferase fusion protein containing the N-terminal extracellular domain of the GPCR. The sera from the second, third, and fourth production bleed of both rabbits exhibited strong immune response to the peptide as seen in the ELISA assay. The antibodies were affinity purified using a peptide affinity column and are valuable for analyzing the expression of this GPCR in T and B cell development.

Monoclonal antibodies to the receptor can also be generated using conventional hybridoma technology known to one or ordinary skill in the art. Briefly, three mice are immunized with 25 µg recombinant receptor prepared as described in Example 9. Mice are inoculated at 3 week intervals with 20 µg GPCR per mouse (½ subcutaneously and ½ intraperitoneally). Serum collected from each animal after the first inoculation reacts with GPCR as determined by immunoprecipitation. Three days after the final inoculation, mice are sacrificed and the spleens harvested and prepared for cell fusion. Splenocytes are fused with Sp2/0 AG14 myeloma cells (ATCC CRL 1581) with polyethylene glycol (PEG). Following PEG fusion, cell preparations are distributed in 96-well plates at a density of $10^5$ cells per well and selected in hypoxanthine/aminopterin/thymidine (HAT) medium containing 10% fetal calf serum and 100 U/ml interleukin-6. The medium is replaced with fresh HAT medium 10 days after plating. To identify hybridomas producing MAbs which recognize GPCR, hybridoma supernatants are tested for the ability to immunoprecipitate purified recombinant GPCR or to detect GPCR by immunoblotting.

A glutathione-S-transferase (GST) fusion protein of the N-terminal extracellular domain of the GPCR was constructed. The mouse and human GPCRs were cloned into various eukaryotic expression vectors which will allow the overexpression of recombinant mouse and human GPCRs in transfected cells in vitro and in vivo by methods well known to one of ordinary skill in the art. Preferably, the constructs containing the GPCR is transfected into eukaryotic cells; more preferably into mammalian cells. Alternatively, the construct may be used to transform bacterial cells.

Since the GPCR is upregulated by BCR-ABL and can suppress the outgrowth of lymphocytes and fibroblasts (Tables 4A–B), antibodies or drugs can be screened which can activate the action of the GPCR to delay the progression of leukemia. In vitro screening assays can be used to find drugs or natural ligands which bind to and activate the GPCR to delay the progression of leukemia. These drugs or antibodies which inhibit the growth of lymphocytes may also be useful for treatment of diseases such as lymphoma or autoimmune diseases.

Conversely, monoclonal antibodies can be generated against particular regions of GPCRs which block the GPCRs and stimulate the growth of normal lymphocytes in vivo. In addition, in vitro screening assays can be used to find drugs or natural ligands which bind to and either activate or inactivate the GPCR. These antibodies, drugs or natural ligands can stimulate the growth of lymphocytes, which may in turn cure or alleviate the symptoms of patients who have either inherited immunodeficiency diseases or Acquired immune deficiency syndrome (AIDS). For example, patients with severe combined immune deficiency (SCID), DiGeorge syndrome, or Bare lymphocyte syndrome lack T cells, and patients with X-linked agammaglobulinemia lack B cells. The antibodies, drugs, natural ligands can be delivered into these patients to inhibit the GPCR to stimulate the growth of the T and B cells in their immune system.

In a preferred embodiment, the cDNA encoding the GPCR is placed in a eukaryotic expression vector for transfection into or infection of a mammalian cell line. Many such cell lines are known in the art, including NIH 3T3, Rat-1, 293T, COS-1, COS-7 and Chinese hamster ovary (CHO) cells, most of which are available from the American type Culture Collection (ATCC), Rockville, Md. Many such expression vectors are known and are commercially available. Preferred expression vectors include retroviral vectors, adenoviral vectors and SV40-based vectors. The vector may contain a selectable marker, such as antibiotic resistance, to select for cells which are expressing the receptor. Alternatively, the expression of the GPCR can be under the control of a regulatory promoter. Stable transfectants are used to screen large libraries of synthetic or natural compounds to identify compounds which bind to the GPCR. Compounds which bind to the GPCR are then tested in the assays described in Examples 7, 10, 11 and 12 to determine whether they are agonists or antagonists of BCR-ABL-mediated GPCR activation.

In one embodiment of the invention, a compound to be tested is radioactively, colorimetrically or fluorimetrically labeled using methods well known in the art and incubated with the receptor. After incubation, it is determined whether the test compound is bound to the receptor. If so, the compound is a potential agonist or antagonist. Functional assays are performed to determine whether the receptor activity is activated or inhibited. These assays include fibroblast and bone marrow transformation assays, cell cycle analysis and in vivo tumor formation assay. Responses can also be measured in cells expressing the receptor using signal transduction systems including, but not limited to, protein phosphorylation, adenylate cyclase activity, phosphoinositide hydrolysis, guanylate cyclase activity, ion fluxes (i.e. calcium) and pH changes. These types of responses can either be present in the host cell or introduced into the host cell along with the receptor.

Because the GPCRs are induced by protein tyrosine kinase oncogenes, they can be used as a diagnostic marker for many types of cancer including leukemia. The DNA sequence can also be used as a probe to search for additional closely-related family members which may play similar roles in oncogenesis.

GPCRs are not expressed in normal bone marrow cells, but are expressed in spleen. Thus, It is possible that GPCRs regulate blood cell development. Regulation of the activity of the GPCR (by antibodies, inhibitory or stimulatory drugs, or natural ligands) may be clinically useful in restoring the normal number and function of the blood cell population with suppressed hematopoiesis, such as that which occurs after treatment to obtain immune depression for organ transplants or after cytotoxic cancer therapy.

The expression of the GPCR in heart suggests that this gene may play a physiological role in heart. It has been shown that there are a variety of autoantibodies, including antireceptor autoantibodies, in patients with cardiomyopathy (Fu, *Mol. Cell. Biochem.* 163:343–7 (1996). Patients with cardiomyopathy may have autoantibodies against the GPCR which contribute to the pathogenesis of cardiomyopathy. Therefore, regulation of GPCR function by neutralizing antibodies, drugs, or natural ligands may alleviate the symptoms of patients with cardiomyopathy. The GPCRs may also be involved in cardiovascular, hypertension-related, cardiac function defects. Regulation of GPCR function by neutralizing antibodies, drugs, or natural ligands may alleviate the symptoms in patients with such defects.

Since we have isolated both murine and human GPCRs, the cDNAs can be used to isolate the homologue of the GPCRs in other species. Identification of the homologues in other species may lead to a cure for the diseases mentioned above in animals, and will therefore have broad applications in veterinary medicine. The amino acid sequence information of the highly conserved regions of the murine and human GPCRs can be used to develop antibodies or drugs that can be used to treat diseases in both human and animals.

The following examples describe the cloning of the murine and human WT BCR-ABL-induced GPCR.

EXAMPLE 1

Plasmid Constructs, Cell Lines, Preparation of Viral Stocks, Generation of Antibodies The WT p185 BCR-ABL and the SH2 mutant were cloned into the pSRαMSV vector (Muller et al., *Mol. Cell. Biol.* 11:1785–1792. 1991) under the control of the LTR promoter as previously described (Afar et al., *Science* 264:424–426, 1994; Pendergast et al., *Cell* 75:175–185, 1993). The pSRαMSV vector was used to produce helper-free retroviral stocks by transient transfection of 293T cells along with the Ψ⁻ packaging vector (Pear et al., *Proc. Natl. Acad. Sci. U.S.A.*, 90:8392–8396, 1993; Afar et al., *Science* 264:424–426, 1994). A 13-amino acid peptide (KDSEETHLPTELS; SEQ ID NO: 5) corresponding to the C-terminal intracellular portion of the murine GPCR was synthesized and injected into rabbit for antibody production (Babco, Berkeley, Calif.). Five production bleeds were obtained. To generate the antibodies against the murine N-terminal extracellular portion of the GPCR, a GST-Mu-GPCR-N fusion construct was made by PCR using GST-Mu-N2A-N5' and GST-Mu-N2A-N3' primers (See Table 2).

Briefly, PCR was performed in a total of 100 µl reaction mixture containing 20 ng template, 30 µl 3.3×XL buffer (Perkin Elmer, Norwalk, Conn.), 6 µl 25 mM magnesium acetate, 2 µl dNTPs (10 mM each nucleotide), 20 pmol of GST-Mu-N2A-N5' and GST-Mu-N2A-N3' primers, and 1 µl rTth polymerase (Perkin Elmer). The cycling conditions were 95° C. for 5 min, 30 cycles of denaturation at 94° C. for 0.5 min, annealing at 56° C. for 1 min and elongation at 72° C. for 1 min. After incubation at 72° C. for 10 min, the amplified PCR fragment was digested with BamHI and EcoRI (Boehringer Mannheim, Indianapolis, Ind.) in Buffer B (10 mM Tris, 5 mM $MgCl_2$, 100 mM NaCl, 1 mM β-mercaptoethanol, pH 8.0, Boehringer Mannheim), and fractionated on an agarose gel. The DNA fragment was excised, purified using Geneclean™ (Bio 101, La Jolla, Calif.) and cloned into the pGEX-2T vector (Pharmacia Biotech) at the BamHI/EcoRI sites. Approximately 50 ng pGEX-2T BamHI/EcoRI fragment was ligated to the PCR product at a 1:3 molar ratio in 1×T4 DNA ligase buffer (50 mM Tris-HCl (pH 7.8), 10 mM $MgCl_2$, 10 mM DTT, 1 mM ATP, 50 µg/ml BSA) and 1 µl T4 DNA ligase (New England Biolabs, Beverly, Mass.) in a 10 µl reaction volume at 16° C. overnight. Transformation was performed by mixing 10% of the ligation reaction with 100 µl of DH5 α competent *E. coli* cells on ice for 20 min. After heat shock at 42° C. for 2 min and incubation on ice for 2 min, 1 ml TYE was added and the transformed cells were further incubated at 37° C. for 1 hr. The transformation mix was plated out on TYE plates containing ampicillin (50 µg/ml). One positive clone containing the insert was identified. The plasmid was sequenced to ensure the proper fusion of the murine N-terminal extracellular portion of GPCR to GST.

EXAMPLE 2

Isolation of cDNA From Bone Marrow Cells

Total RNA was isolated from primary murine bone marrow cells transformed by a retrievers encoding either the WT p185 BCR-ABL or the SH2 mutant variant (Goga et al., *Cell* 82:981–988, 1995) using the Ultraspec RNA isolation system (Biotecx Laboratories, Inc., Houston, Tex.). Polyadenylated RNA was purified from total RNA using oligo (dT) cellulose columns (Collaborative Research) according to the manufacturer's instructions. cDNA was synthesized using SuperScript choice system (GibcoBRL Life Technologies, Gaithersburg, Md.), according to the manufacturer's protocols.

EXAMPLE 3

Representational Difference Analysis (RDA) and DNA Sequencing

To isolate genes that were differentially regulated by the WT p185 BCR-ABL, but not by the SH2 mutant variant, a modified version of a PCR-based subtractive-hybridization technique called Representational Difference Analysis (RDA) was used. RDA was originally developed to detect differences between two complex genomes (Lisitsyn et al., *Science*, 259:946–951, 1993). It was later adapted for use with cDNA and has been used successfully to isolate differentially expressed genes in various systems (Hubank et al., *Nucl. Acids Res.* 22:5640–5648, 1994; Braun et al., *Mol. Cell. Biol.* 15:4623–4630 (1995). The cDNA sample containing the genes of interest is termed the tester, and the sample used for subtraction is the driver. Both the tester and driver cDNAs are digested with a restriction enzyme, DpnII, then ligated to RBgl adapters (the RBgl12 and RBgl24 primers, see Table 2) for PCR amplification. The RBgl adapters were then removed. To isolate differentially-expressed genes, the amplified tester DNA is ligated to new adapters, JBgl adapters (the JBgl 12 and JBgl 24 primers, see Table 1) and mixed with the driver DNA in a subtractive hybridization. The differentially-expressed genes form tester-tester homo-duplexes and can be preferentially amplified by PCR using the JBgl24 primer. This process is repeated three times, with increasing ratios of driver to tester from 1:100, 1:800, to 1:8000 during subtractive hybridization (Lisitsyn et al., supra.; Hubank et al., supra.).

In this study, cDNA from HDBM cells transformed by the WT p185 was used as the tester and that by the SH2 mutant as the driver to isolate genes that are upregulated by the WT p185 BCR-ABL. RDA was also performed in parallel using the SH2 mutant as the tester and the WT as the driver to isolate genes that are downregulated by the WT p185. The differentially amplified gene fragments were then digested with DpnII and cloned into the BamHI site of the pBluescript cloning vector (Stratagene, La Jolla, Calif.). DNA sequencing was then performed using ABI PRISM Dye Terminator Cycle Sequencing Ready Reaction Kit (Perkin Elmer) or Sequenase version 2.0 DNA sequencing kit (United States Biochemical, Cleveland, Ohio). After sequencing the clones from both directions, the sequence information was used to search databases using the BLAST program. Both the protein database (non-redundant updated protein database PDB+SwissProt+PIR) and nucleotide database (PDB+GenBank+EMBL) were searched. Sequence analysis of a 377 base-pair DNA fragment of a partial murine GPCR clone (N2A) revealed that it was a novel GPCR homologous to multiple GPCR family members in the database.

TABLE 1

Oligonucleotides used for RDA

| RBgl24 | AGCACTCTCCAGCCTCTCACCGCA | (SEQ ID NO: 6) |
|---|---|---|
| JBgl24 | ACCGACGTCGACTATCCATGAACA | (SEQ ID NO: 7) |
| NBgl24 | AGGCAACTGTGCTATCCGAGGGAA | (SEQ ID NO: 8) |
| RBgl12 | GATCTGCGGTGA | (SEQ ID NO: 9) |
| JBgl12 | GATCTGTTCATG | (SEQ ID NO: 10) |
| NBgl12 | GATCTTCCCTCG | (SEQ ID NO: 11) |

EXAMPLE 4

Isolation of Mouse GPCR cDNA and Genomic Clones

The 377 bp N2A fragment was used as a probe to screen a mouse spleen cDNA library (Clontech, Palo Alto, Calif.) according to the manufacturer's instructions. Briefly, *E. coli* strain 1090r- was grown in TYE broth in the presence of 10 mM $MgSO_4$ and 0.2% maltose overnight. The library was incubated with overnight *E. coli* culture and then plated out on TYE plates using 0.7% agarose in TYE+20 mM $MgSO_4$. After incubation at 37° C. until plaques were about 1 mm in diameter, the plates were chilled at 4° C. for 1 hr before the filters were placed on the plates. The filters were then lifted and autoclaved at 100° C. for 1 min to denature the DNA. The filters were prehybridized for 4 h in hybridization buffer containing 1% SDS, 2×SSC (20×SSC=3 M NaCl, 0.3 M NaCitrate-2 $H_2O$, pH to 7.0), 10% dextran sulfate, 50% formamide, 1×Denhardt's solution (50×Denhardt's solution=1% ficoll, 1% polyvinylpyrrolidone and 1% BSA, pentax fraction V) and 0.25 mg/ml salmon sperm DNA. The N2A fragment was labeled using Primer-It II Random Primer Labeling Kit (Stratagene). The filters were hybridized overnight at 42° C. with the N2A probe in the hybridization buffer. The filters were washed twice with 2×SSC and 0.1% SDS for a total of 1.5 hrs. One positive clone was identified after screening $1\times10^6$ plaques. Sequence analysis revealed that the clone contained the C-terminal portion of the GPCR. 5'-RACE was then used to obtain the N-terminal portion of the gene using 5' RACE system (GibcoBRL) according to the manufacturer's instruction. Briefly, the N2AGSP1 primer (see Table 2) was used to prime first-strand cDNA synthesis. After purification of first-strand cDNA and homopolymer addition of dCTP by terminal deoxynucleotidyl transferase (TdT) to the cDNA at the 3' end, a nested primer, N2AGSP2 (see Table 2) that anneals to sequences located 3' of N2AGSP1 and the 5' RACE anchor primer (see Table 2) were used for PCR amplification of the N-terminal fragment of the murine GPCR. The PCR was performed in a 50 µl reaction mixture containing 20 mM Tris-HCl (pH 8.4), 50 mM KCl, 1.5 mM $MgCl_2$, 200 uM each dNTP, 100 nM N2AGSP2 primer and 100 nM anchor primer. The dC-tailed cDNA was first denatured at 94° C. for 5 min. After addition of 2 units Taq DNA polymerase, PCR was performed by 35 cycles of denaturation at 94° C. for 0.5 min, annealing at 62° C. for 1 min and elongation at 72° C. for 3 min.

After obtaining the sequence information of the N-terminal portion of the gene, a full length clone was obtained by RT-PCR (3' RACE system, GibcoBRL) using total RNA isolated from bone marrow cells transformed by the WT BCR-ABL. The primers for generation of full length murine GPCR were N2A 3' RACE-1 (5' primer) and MuN2A3'-2 (3' primer) (see Table 2). Briefly, PCR was performed in a 50 μl reaction mixture using the rTth DNA polymerase system (Perkin Elmer) containing 1×XL buffer, 1.5 mM magnesium acetate, 10 pmol of each primer, 2 μl of first strand cDNA synthesis product, 0.2 mM dNTPs and 0.5 μl of rTth polymerase (Perkin Elmer). The cycling conditions were 94° C. for 3 min, 35 cycles of denaturation at 94° C. for 0.5 min, annealing at 62° C. for 1 min and elongation at 72° C. for 3 min. The amplified PCR fragments were fractionated on an agarose gel. The approximately 1.3 kb fragment containing the full length murine GPCR cDNA (SEQ ID NO: 1) was excised, purified using Geneclean™ and subcloned into the pCRII vector (Invitrogen, San Diego, Calif.). Multiple clones were sequenced using N2AGSP2, N2Arandom, N2A5, T7, and M13 Reverse primers (see Table 2). To create a hemagglutinin (HA)-tag version of murine GPCR, PCR was performed using the MuN2A-HA-N and MuN2A-HA-C primers (see Table 2). The amplified PCR fragment was subcloned into the pCRII vector (Invitrogen). The insert was then excised with XhoI and NotI and subcloned into the pGD retroviral expression vector at the XhoI and NotI site. Multiple PCR clones were sequenced from both directions to ensure the in-frame fusion of the GPCR with the HA-tag engineered at the NotI site of the pGD expression vector.

To obtain the mouse GPCR genomic clone, the mouse GPCR cDNA was used as a probe to screen a mouse genomic library. The library was made with genomic DNA from mouse strain 129. The genomic DNA was partially digested with MboI, size-fractionated (17–21 kb), and ligated into the BamHI site of DashII arms (Stratagene). At least one positive clone was isolated and the authenticity of the clone was verified by direct sequencing of the genomic DNA and by PCR analysis using primers specific for the gene.

TABLE 2

Oligonucleotides used in the analysis of Murine GPCR

| Primer | Sequence, 5'–3' | |
|---|---|---|
| MuN2A3'RACE-1 | CAGGACTGGCTTGGGTCATT | (SEQ ID NO: 12) |
| MuN2A3'RACE-2 | GTCCACAGAACTCACATAGGA | (SEQ ID NO: 13) |
| MuN2A3'-1 | CGCGGATCCGAATTCGGTACCGGTGACTCAGAGGACCAG | (SEQ ID NO: 14) |
| MuN2A-HA-N | CGGAATTCTCGAGTCAGGACTGGCTTGGGTCATT | (SEQ ID NO: 15) |
| MuN2A-HA-C | ATAGTTTAGCGGCCGCGCAGAGCTCCTCAGGCAGT | (SEQ ID NO: 16) |
| Mu+HuN2A+8 | CAAGAAGTGTCCAGAATCCA | (SEQ ID NO: 17) |
| N2AGSP1 | GGTGACAGCAGTCCTCTGGT | (SEQ ID NO: 18) |
| N2AGSP2 | TAGCGGTCGCAGGAAATGCAG | (SEQ ID NO: 19) |
| N2Arandom | TGATTGGTGAACGCCAGG | (SEQ ID NO: 20) |
| N2A5 | GCTTTGAGCCCCTGAGGATGAA | (SEQ ID NO: 21) |
| T7 | GTAATACGACTCACTATAGGGC | (SEQ ID NO: 22) |
| GST-Mu-N2A-N5' | GTCGGATCCATGAGATCAGAACCTACCAAT | (SEQ ID NO: 23) |
| GST-Mu-N2A-N3' | GTCGAATTCTCACAGGACCACTCTGCTCTC | (SEQ ID NO: 24) |
| M13 Reverse | CAGGAAACAGCTATGAC | (SEQ ID NO: 25) |
| Anchor Primer | CUACUACUACUAGGCCACGCGTCGA-CTAGTACGGGIIGGGIIGGGIIG | (SEQ ID NO: 26) |
| MuN2A3'HA | GCCGAATTCTCAAACTCCGGC | (SEQ ID NO: 27) |
| MuN2Aflag5 | CCGGAATTCGGCCACCATGGACTACAAGGACGACGATG-ACAAGAGATCAGAACCTACCAATGCA | (SEQ ID NO: 28) |
| MuN2A5'Eco | CCGGAATTCCTAGAGGCCACCATGAGATCAGAACCTAC-CAAT | (SEQ ID NO: 29) |

EXAMPLE 5

Isolation of Human GPCR cDNA and Genomic Clones

The murine GPCR was used as a probe to screen a human spleen cDNA library (ClonTech, Palo Alto, Calif.) to isolate the human homologue. The probe was labeled as described above. The hybridization was performed in Rapid-hyb buffer (Amersham Life Science, Arlington Heights, Ill.) for 2 hrs at 65° C. The filters were washed twice with 2×SSC and 0.1% SDS at 65° C. for a total of 40 mins. At least four positive clones were isolated after screening 1.5×10$^6$ plaques. Sequence analysis revealed that these were overlapping clones containing an open reading frame encoding a protein of 380 amino acids with a calculated molecular weight of 42 kD. Multiple clones were sequenced from both directions to ensure the accuracy of the sequence. PCR was then used to amplify the full length human GPCR from the human spleen cDNA library using the gene-specific primers HuN2A+N1HA (5' primer) and HuN2A-C (3' primer) (see Table 3). To generate a HA-tag version of human GPCR, the 5' primer HuN2A+N1HA and 3' primer HuN2A-HA-C were used (see Table 3). The amplified PCR fragment containing the full length human GPCR cDNA (SEQ ID N: 3) was purified using Geneclean™ and cloned into the pCRII vector. Multiple clones were sequenced using T7, SP6, N2AGSP2, Mu+HuN2A+8, HuN2AE+2A, HuN2AC-8, and HuN2A+6 primers (Table 2) to ensure the accuracy of the sequence. Alignment of the mouse and human GPCRs show that they are about 70% identical to each other at the amino acid level.

SH2 mutant variant. The cells were plated at a density of $5 \times 10^6$ cells per 6-cm dish in RPMI containing 10% fetal bovine serum and β-mercaptoethanol as previously described (McLaughlin et al., *Mol. Cell. Biol.* 9:1866–1874, 1989). The viral stocks were prepared as described (Goga et al., *Cell* 82:981–988, 1995).

EXAMPLE 8

Regulation of GPCR Transcription During B and T Cell Activation

Human B cells (Ramos) and T cells (Jurkat) were grown in RPMI 1640 containing 10% fetal calf serum to a density

TABLE 3

Oligonucleotides used in the analysis of human GPCR

| Primer | Sequence, 5'-3' | |
|---|---|---|
| HuN2A+N1HA | CGCTCGAGTGGGAGCAAATGCGGAGCGAG | (SEQ ID NO: 30) |
| HuN2A-C | TTAGCGGCCGCTCAGCAGGACTCCTCAATCAG | (SEQ ID NO: 31) |
| Hun2A-HA-C | TTAGCGGCCGCGCAGGACTCCTCAATCAGCCTC | (SEQ ID NO: 32) |
| Mu+HuN2A+8 | CAAGAAGTGTCCAGAATCCA | (SEQ ID NO: 33) |
| HuN2A+9 | ACCAGCCACAGTGCCCATG | (SEQ ID NO: 34) |
| HuN2AE+2A | TGCCACTCTGGGTCATCTAT | (SEQ ID NO: 35) |
| HuN2A+6 | CGGTGGTTGTCATCTTCCTA | (SEQ ID NO: 36) |
| T7 | GTAATACGACTCACTATAGGGC | (SEQ ID NO: 37) |
| M13 Reverse | CAGGAAACAGCTATGAC | (SEQ ID NO: 38) |

EXAMPLE 6

Northern Analysis

RNA was purified using the Ultraspec RNA isolation system (Biotecx laboratories, Inc., Houston, Tex.). To examine the expression level of a gene of interest, a DNA fragment of the gene was labeled using the Prime-it II random primer labeling kit (Stratagene). Northern blotting was performed as previously described (Schneider at al., *Cell* 54:787–793, 1993). Briefly, the RNA samples were fractionated in an agarose gel (1% agarose, 20 mM phosphate, pH 7.0, 7% formaldehyde), transferred to Nitro-Pure nitrocellulose transfer membrane (Micron Separations, Inc. Westborough, Mass.) using 20xSSC. The blot was baked at 80° C. for 2 h and prehybridized in the prehybridization buffer (50% formamide, 5xSSC, 1xDenhardt's, 50 mM phosphate stock buffer and 0.25 mg/ml salmon sperm DNA) for 4 h. The blot was then hybridized overnight at 42° C. with the probe in 8 ml prehybridization buffer and 2 ml 50% dextran sulfate. The blot was washed once with 2xSSC, 0.1% SDS at room temperature for 30 min, and once with 2xSSC, 0.1% SDS at 60° C. for 30 min. The blot was exposed to x-ray film at −70° C.

EXAMPLE 7

Murine Bone Marrow Transformation Assay and Reconstitution of Irradiated Mice

Fresh bone marrow cells from the tibias and femurs of 3- to 4-week-old BALB/c mice were isolated and infected with retrovirus encoding either the WT BCR-ABL p185 or the of $2 \times 10^6$ cells/ml. The cells were resuspended at a density of $2 \times 10^8$ cells/ml in serum-free RPMI immediately prior to stimulation. For activation of Ramos cells with anti-IgM, goat anti-IgM was added to cell suspensions (0.5 ml) at a final concentration of 10 μg/ml. After 0 min, 5 min, 7 hours and 24 hours at 37° C., RNA was isolated.

For activation of Ramos and Jurkat cells with ionomycin and PMA, ionomycin and PMA were added to the cells to a final concentration of 2 μg/ml and 20 ng/ml, respectively, and RNA was isolated at 0, 3, 6, 24 and 48 hours. For activation of Jurkat cells by anti-CD3 and CD28 antibodies, respectively, each 10 cm plate was coated with anti-CD3 (6.25 μg) and anti-CD28 (12.5 μg) antibodies (Sigma, St. Louis, Mo.). The Jurkat cells were subsequently seeded onto the antibody-coated plates. The cells were harvested at 0, 3, 6, 24 and 48 hours after activation and RNA was isolated.

For RT-PCR, 5 μg total RNA from each sample was used to synthesize the first strand cDNA using the Superscript™ preamplification system (GIBCO BRL). Ten percent of the first strand cDNA synthesis product was then used for PCR. The HuN2A-C1 (SEQ ID NO: 28) and HuN2A+6 (SEQ ID NO: 33) primers were used for amplification of the human GPCR fragment. A control set of primers, G3PDH control amplimers set for human and mouse (5'-ACCACAGTCCATGCCATCAC-3'; SEQ ID NO: 39 and 5'-TCCACCACCCTGTTGCTGTA; SEQ ID NO: 40), were used to ensure that equal amounts of template were used. PCR was performed in a 50 μl reaction mixture containing 1xPCR buffer (20 mM Tris-HCl, pH 8.4, 50 mM KCl; GIBCO), 1.5 mM $MgCl_2$, 0.4 mM of each dNTP, 10 pmol of each primer, 0.5 μl Taq DNA polymerase (GIBCO) and 2 μl of first strand cDNA synthesis product. The cDNA was denatured at 94° C. for three minutes. PCR was performed by 35 cycles of denaturation at 94° C. for 0.5 min, annealing at 58° C. for 1 min, and elongation at 72° C. for 2 min.

The human GPCR was found to be transcriptionally upregulated in B cells upon activation by anti-IgM antibody, suggesting that B cell receptor activation upregulates transcription of GPCR. Upregulation of the GPCR transcript was also observed in response to receptor-independent activation of intracellular signaling pathways. The simultaneous addition of ionomycin and PMA to B cells to increase the intracellular calcium levels and to activate Protein Kinase C, respectively, resulted in increased levels of GPCR mRNA. Activation of Ramos cells with CD40 ligand also upregulated the GPCR transcript. In addition, exposure of Ramos cells to x-ray irradiation, a process which induces DNA damage and cell cycle arrest, also induced the transcription of GPCR. However, no dramatic alteration in GPCR transcript levels was observed in Jurkat cells upon activation by PMA plus ionomycin or anti-CD3 plus CD28 antibodies. These data suggest that the human GPCR may play a role during B cell activation. As a control, glyceraldehyde 3-phosphate dehydrogenase (G3PDH) control amplimer set was used to ensure that equal amounts of templates were used for RT-PCR. Taken together, these results suggest that the GPCR may play a role upon B cell activation. The transcriptional activation of GPCR may either be involved in apoptosis of B cells or proliferation and/or differentiation of B cells.

EXAMPLE 9

Insertion of Mouse and Human GPCRs into Expression Vectors

GPCR cDNA was inserted into several eukaryotic expression vectors. Any of these constructs can be used to transfect eukaryotic cells, preferably mammalian cells, for production of recombinant GPCR using methods well known in the art. Such methods are described in, for example, Sambrook et al. (*Molecular Biology: a Laboratory Manual*, Cold Spring Harbor Laboratory, 1988; Ausubel, *Current Protocols in Molecular Biology*, 1989). Such eukaryotic cells include Rat-1, NIH 3T3, 293T, CHO, COS-7 and BHK cells. The GPCR can also be inserted into a baculovirus expression vector which is used to infect Sf9 insect cells using methods well known in the art.

N-terminal flag-tagged mouse GPCR in the pCRII vector (Invitrogen) was used for in vitro transcription and translation of mouse GPCR and for making probes for Northern, S1 or in situ analysis. Reverse transcription of RNA into first strand cDNA was performed using RNA isolated from bone marrow cells transformed with WT BCR-ABL. PCR was performed using 10 pmol of MuN2Aflag5 and MuN2A3'-1 primers (Table 2) in 50 µl reaction mixture containing 1×pfu buffer (20 mM Tris-HCl, pH 8.75, 10 mM KCl, 10 mM (NH$_4$)$_2$SO$_4$, 2 mM MgSO$_4$, 0.1% Triton X-100, 100 µg/ml BSA) (Sigma). The cDNA was first denatured at 94° C. for 3 min. PCR was performed by 35 cycles of denaturation at 94° C. for 0.5 min., annealing at 62° C. for 1 min. and elongation at 75° C. for 3 min. The amplified PCR product was cloned into the pCRII vector (Invitrogen) according to the manufacturer's instructions.

The pSRα-Flag-GPCR tk Neo expression vector is a retroviral expression vector for expression of mouse and human GPCRs in mammalian cells. In this construct, the Neo gene is under control of the herpes simplex virus thymidine kinase (tk) promoter for selection of infected cells with G418. The EcoRI insert from pCRII-Flag-Mu-GPCR was excised and cloned into pSRα-Flag-GPCR tk Neo at the EcoRI cloning site upstream of the TK promoter.

pCRII-Mu-GPCR, the untagged version of pCR-Flag-Mu-GPCR, was used for in vitro transcription and translation, and for making probes for Northern, S1 or in situ analysis. For construction of this vector, RT-PCR was performed using primers MuN2A5'Eco and MuN2A3'-1(Table 2) using the protocol described for pCRII-Mu-GPCR. The amplified PCR product was cloned into the pCRII vector. In vitro transcription and translation were performed using the TNT-coupled reticulocyte lysate system (Promega, Madison, Wis.) according to the manufacturer's instructions. The in vitro transcription and translation of Mu-GPCR revealed a protein product having a molecular weight of about 42 kDa which is similar to the calculated molecular weight of mouse GPCR.

pCRII-Mu-GPCR-HA, the C-terminal HA-tagged version of mouse GPCR was used for in vitro transcription/translation and for labeling proves for Northern, S1 or in situ analysis. For construction of this vector, RT-PCR was performed using primers MuN2A5'Eco and MuN2A3'HA using the plasmid vector pGD-Mu-GPCR-HA containing the HA-tagged version of murine GPCR. The PCR product was cloned into the pCRII vector (Invitrogen).

For construction of pMu-GPCR-GFP, the mouse GPCR was fused to the N-terminal green fluorescence protein (GFP) in the pEGFP vector (Clontech). The murine GPCR was amplified using primers specific for murine GPCR and fused in frame with GFP in the pEGFP vector. The expression of the Mu-GPCR-GFP fusion protein was confirmed by FACS analysis. The fusion protein will allow following the expression of murine GPCR in mammalian cells and functional analysis of the GPCR. Similarly, for pEGF-Hu-GPCR-GFP, human GPCR was fused to the N-terminal green fluorescence protein (GFP) in the pEGFP vector. The human GPCR is amplified using primers specific for human GPCR and fused in frame with GFP in the pEGFP vector. The fusion protein allows following the expression of human GPCR in mammalian cells and functional analysis of the GPCR.

EXAMPLE 10

Acceleration of Leukemogenesis in vivo by GPCR

One day prior to reconstitution, severe combined immunodeficient (SCID) mice were sublethally irradiated with 275 rads. Whole bone marrow was isolated and infected with retrovirus as described above. Three hours post-infection, the bone marrow was injected intravenously into the tail veins of recipient SCID mice. Animals are monitored for signs of sickness over a twelve-week period. Sick mice are sacrificed and tissues are analyzed for BCR-ABL expression by Western Blotting. Blood and spleen samples are analyzed by fluorescence activated cell sorting (FACS). Blood smears are analyzed by Wright/Giemsa staining. Mice which were injected with WT BCR-ABL exhibit significantly more leukemogenesis than mice injected with the SH2 mutant.

Since the GPCR is induced by the WT-BCR-ABL in bone marrow cells, its effect on transformation by BCR-ABL was evaluated as described below.

EXAMPLE 11

The GPCR Functions as a Tumor Suppressor Gene

The GPCR, GPCR-GFP, or GFP indicator cell lines were generated by infection of Rat-1 fibroblasts with helper-free retroviruses followed by selection in G418 (0.4 mg/ml) for approximately 1–2 weeks. The expression of GPCR-GFP and GFP were confirmed by FACS analysis using a FACScan (Becton Dickinson). Transformation by various oncogenes was measured using a soft agar assay as described (Lugo et al., Mol. Cell Biol. 9:1263–1270, 1989). Briefly, the indicator cell lines were plated at a density of $6 \times 10^4$ cells/6 cm dish overnight. Infection was performed for 3 hours at 37° C. using 1 ml of virus stock with 8 μg/ml polybrene. Two days post-infection, cells were plated in agar at a density of $1 \times 10^4$ cells/6 cm dish in duplicate. Dishes were re-fed at one week and colonies were counted after three weeks. Colonies greater than 0.5 mm in diameter were scored positive.

As listed in Tables 4A–B, overexpression of GPCR suppressed the number of agar colonies induced by BCR-ABL p185 approximately five fold. GPCR epitope-tagged with GFP still retained some ability to block BCR-ABL-mediated transformation in Rat-1 cells. GPCR also blocked agar colonies induced by Gag-BTK*, an activated version of Bruton tyrosine kinase, and the transcription factor Myc. Interestingly, GPCR failed to block transformation mediated by v-ABL or the serine kinase oncogene v-Mos. v-ABL and v-Mos may transform cells by mechanisms distinct from BCR-ABL, Myc and Gag-BTK*. Since BTK has been shown to play a critical role in B cell development (Tsukada et al., Cell 72:279–290, 1993; Rawlings et al., Immunological. Rev. 138, 1994), the ability of GPCR to block Gag-BTK* transformation also suggests that the GPCR may also be a regulator of BTK during B cell development. Similarly, overexpression of the GPCR gene suppressed the transformation of bone marrow cells. In addition, in vivo tumor formation and leukemogenesis assays can be used to analyze the effect of GPCR on malignant phenotypes induced by various organisms.

TABLE 4A

| Oncogene | Rat-1 | Rat-1/GPCR |
|---|---|---|
| φ | 0 | 0 |
| BCR-ABL p185 | >1300 | 226 ± 40 |
| v-ABL | 552 ± 28 | 444 ± 24 |
| Myc | >1300 | 388 ± 20 |

TABLE 4B

| Oncogene | Rat-1/GFP | Rat-1/GPCR-GFP |
|---|---|---|
| φ | 9 ± 1 | 2 ± 1 |
| BCR-ABL p185WT | >1300 | 608 ± 40 |
| v-ABL | 432 ± 64 | 496 ± 16 |
| Gag-BTK* | 88 ± 12 | 3 ± 1 |
| v-Mos | 224 ± 16 | 172 ± 20 |

To determine whether the GPCR was involved in the regulation of cell cycle progression, Rat-1 fibroblasts were infected with retrovirus expressing the GPCR gene as described in the following example.

EXAMPLE 12

GPCR Induces Cell Cycle Arrest During Mitosis

Rat-1 cells were selected with G418 (0.4 mg/ml) for one week and grown to either subconfluence or confluence. The cells were harvested by trypsinization and pelleted by centrifugation. The cells were then resuspended in Vindelov's stain (5 mM Tris, pH 7.4, 5 mM NaCl, 0.05% NP-40, 0.04 mg/ml propidium iodide, 5 μg/ml RNase) and incubated on ice for 15 min in the dark. Flow cytometric analysis was performed using FACScan (Lysis II program). As shown in Table 5, expression of the GPCR appears to increase the percentage of cells in the G2/M phase of the cell cycle. Examination of Rat-1 cells expressing the GPCR under the microscope revealed a higher percentage of cells with bi- or poly-nuclei (approximately 5–10% versus less than 1% observed in parental Rat-1 cells), suggesting that GPCR-expressing cells were likely to be arrested at the anaphase of mitosis. Taken together, these data suggest that the GPCR may function as a tumor suppressor gene and is involved in cell cycle arret during mitosis. The biological properties of the GPCR share similarities with p53, a tumor suppressor gene. Both GPCR and p53 negatively regulate cell growth and induce cell cycle arret. Interestingly, their expressions are both upregulated by DNA damage-inducing agents such as X-rays. The ability of certain oncogenes to induce the expression of GPCR and the ability of GPCR to block the oncogenic potential of these genes suggest that the GPCR may comprise a self-defense mechanism for cells to counter ill-fated transformation phenotypes.

TABLE 5

|  | G1 | S | G2/M | dead cells |
|---|---|---|---|---|
| Rat-1 (subconfluent) | 60% | 14% | 25% | 1% |
| Rat-1/GPCR (subconfluent) | 47% | 14% | 37% | 2% |
| Rat-1 (confluent) | 64% | 11% | 24% | 1% |
| Rat-1/GPCR (confluent) | 49% | 12% | 36% | 3% |

EXAMPLE 13

Chromosomal Localization of Human GPCR

Fluorescence in situ hybridization (FISH) was performed using human metaphase cells prepared from phytohemag-glutinin (PHA)-stimulated peripheral blood lymphocytes. The GPCR probe was a human genomic fragment cloned into the Lambda DASH vector (Stratagene) at the SAlI site. FISH was performed as described by Rowley et al. (Proc. Natl. Acad. Sci. U.S.A. 87:9368–9372, 1990). A biotin-labeled probe was prepared by nick-translation using Bio-16-dUTP (Enzo diagnostics). Hybridization was detected with fluorescein-conjugated avidin (Vector Laboratories, Burlingame, Cailf.), and chromosomes were identified by staining with 4,6-diamidino-2-phenylindole-dihydrochloride (DAPI). The human GPCR was found to be localized to chromosome 14, band q32.3. It has been shown that chromosomal abnormalities at 14q32.3 are associated with a wide variety of human cancers. For example, rearrangements of bands 14q32.3 and 19p13.3 were found in patients with multiple myeloma and plasma cell leukemia (Taniwaki et al., Leukemia and Lymphoma 21:25–30, 1996; Fujino et al., Cancer Res. 55:3246–3249, 1995). In addition, deletion mapping analysis has strongly suggested that loss of a putative tumor suppressor gene at 14q32 may be involved in the pathogenesis of ovarian, endometrial, colorectal and bladder cancers (Bandera et al., Cancer Res. 57:513–515). Chromosomal abnormalities have also been reported at 14q32 in other human diseases such as desmoplastic infantile ganglioma and mantle cell lymphomas (Bergsagel, Proc. Natl. Acad. Sci. U.S.A. 93:13931–13936, 1996; Vaandrager et al., Blood 88:1177–1182, 1996). Based on the ability of GPCR to suppress transformation phenotypes of oncogenes, GPCR is a candidate tumor suppressor gene whose loss of expression may be at least partially involved in the progression of certain cancers.

It should be noted that the present invention is not limited to only those embodiments described in the Detailed Description. Any embodiment which retains the spirit of the present invention should be considered to be within its scope. However, the invention is only limited by the scope of the appended claims.

What is claimed is:

1. An isolated polynucleotide having the nucleotide sequence shown in SEQ ID NO: 1 or 3.

2. An isolated, recombinant GPCR having the amino acid sequence shown in SEQ ID NO: 2 or 4.

3. The protein having the amino acid sequence shown in the SEQ ID NO: 2of claim 2, wherein said protein is obtained by expression of a polynucleotide having the sequence shown in SEQ ID NO: 1.

4. The protein having the amino acid sequence shown in the SEQ ID NO: 4 of claim 2, wherein said protein is obtained by expression of a polynucleotide having the sequence shown in SEQ ID NO: 3.

5. An isolated polynucleotide which encodes the protein having the amino acid sequence shown in SEQ ID NO: 2.

6. An isolated polynucleotide which encodes the protein having the amino acid sequence shown in SEQ ID NO: 4.

* * * * *

```
                              SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
         (A) LENGTH: 1507 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: Coding Sequence
         (B) LOCATION: 147...1292
         (D) OTHER INFORMATION:

(xi) SEQUENCE DESCRIPTION: SEQ ID NO:1:

AAACCTCCCA GCTGGGCCTG CAGAGGGGTG CTCAGCCCTG CCTCAGGACG GGCCTGCCCT       60

GTGCTGCCTC AGGACTGGCT TGGGTCATTT TAAGCTGCCA GAGCCACCTT CACAAGGGGG      120

TCCACAGAAC TCACATAGGA GCCACC ATG AGA TCA GAA CCT ACC AAT GCA GCA      173
                             Met Arg Ser Glu Pro Thr Asn Ala Ala
                              1               5

GGA AAC ACC ACA CTG GGG GTT ACC TCC GTT CTT CAG AGC ACC TCA GTA       221
Gly Asn Thr Thr Leu Gly Val Thr Ser Val Leu Gln Ser Thr Ser Val
 10              15                  20                  25

CCT TCT TCT GAG ACC TGC CAC GTC TCC TAC GAG GAG AGC AGA GTG GTC       269
Pro Ser Ser Glu Thr Cys His Val Ser Tyr Glu Glu Ser Arg Val Val
                 30                  35                  40

CTG GTG GTG GTG TAC AGT GCC GTG TGC CTG CTG GGC CTA CCA GCC AAC       317
Leu Val Val Val Tyr Ser Ala Val Cys Leu Leu Gly Leu Pro Ala Asn
                     45                  50                  55

TGC CTG ACT GCC TGG CTG ACG CTG CTG CAA GTC CTG CAG AGG AAC GTG       365
Cys Leu Thr Ala Trp Leu Thr Leu Leu Gln Val Leu Gln Arg Asn Val
         60                  65                  70

CTA GCC GTC TAC CTG TTC TGC CTG TCC CTC TGT GAG CTG CTC TAC ATC       413
Leu Ala Val Tyr Leu Phe Cys Leu Ser Leu Cys Glu Leu Leu Tyr Ile
     75                  80                  85

AGC ACG GTG CCA TTG TGG ATC ATC TAC ATC CAG AAT CAG CAC AAA TGG       461
Ser Thr Val Pro Leu Trp Ile Ile Tyr Ile Gln Asn Gln His Lys Trp
 90                  95                 100                 105

AAC CTG GGT CCG CAG GCC TGC AAG GTG ACT GCT TAC ATC TTC TTC TGC       509
Asn Leu Gly Pro Gln Ala Cys Lys Val Thr Ala Tyr Ile Phe Phe Cys
                110                 115                 120

AAC ATC TAC ATC AGC ATC CTC TTG CTC TGC TGC ATT TCC TGC GAC CGC       557
Asn Ile Tyr Ile Ser Ile Leu Leu Cys Cys Ile Ser Cys Asp Arg
                125                 130                 135

TAC ATG GCC GTG GTC TAT GCA CTG GAG AGC CGA GGC CAC CGC CAC CAG       605
Tyr Met Ala Val Val Tyr Ala Leu Glu Ser Arg Gly His Arg His Gln
                140                 145                 150

AGG ACT GCT GTC ACC ATT TCT GCG TGT GTG ATT CTT CTT GTT GGA CTT       653
Arg Thr Ala Val Thr Ile Ser Ala Cys Val Ile Leu Leu Val Gly Leu
        155                 160                 165

GTT AAC TAT CCA GTG TTT GAC ATG AAG GTG GAG AAG AGT TTC TGC TTT       701
```

```
Val Asn Tyr Pro Val Phe Asp Met Lys Val Glu Lys Ser Phe Cys Phe
170                 175                 180                 185

GAG CCC CTG AGG ATG AAC AGC AAG ATA GCC GGC TAC CAC TAC CTG CGT        749
Glu Pro Leu Arg Met Asn Ser Lys Ile Ala Gly Tyr His Tyr Leu Arg
                190                 195                 200

TTC ACC TTT GGC TTT GCC ATC CCT CTC GGC ATC CTG GCG TTC ACC AAT        797
Phe Thr Phe Gly Phe Ala Ile Pro Leu Gly Ile Leu Ala Phe Thr Asn
            205                 210                 215

CAC CAG ATC TTC CGG AGC ATC AAA CTC AGT GAC AGC CTG AGC GCT GCG        845
His Gln Ile Phe Arg Ser Ile Lys Leu Ser Asp Ser Leu Ser Ala Ala
        220                 225                 230

CAG AAG AAC AAG GTG AAG CGC TCC GCC ATC GCG GTC GTC ACC ATC TTC        893
Gln Lys Asn Lys Val Lys Arg Ser Ala Ile Ala Val Val Thr Ile Phe
    235                 240                 245

CTG GTC TGC TTT GCT CCC TAC CAC GTG GTA CTC CTC GTC AAA GCT GCC        941
Leu Val Cys Phe Ala Pro Tyr His Val Val Leu Leu Val Lys Ala Ala
250                 255                 260                 265

AGC TTT TCC TTC TAC CAA GGA GAC ATG GAT GCC GTG TGT GCC TTT GAA        989
Ser Phe Ser Phe Tyr Gln Gly Asp Met Asp Ala Val Cys Ala Phe Glu
                270                 275                 280

AGC AGA CTG TAC ACA GTC TCT ATG GTG TTT CTG TGC CTG TCT ACA GTC       1037
Ser Arg Leu Tyr Thr Val Ser Met Val Phe Leu Cys Leu Ser Thr Val
            285                 290                 295

AAC AGT GTG GCT GAC CCC ATC ATC TAC GTG CTG GGT ACA GAC CAC TCT       1085
Asn Ser Val Ala Asp Pro Ile Ile Tyr Val Leu Gly Thr Asp His Ser
        300                 305                 310

CGG CAA GAA GTG TCC AGA ATC CAC ACA GGG TGG AAA AAG TGG TCC ACA       1133
Arg Gln Glu Val Ser Arg Ile His Thr Gly Trp Lys Lys Trp Ser Thr
    315                 320                 325

AAG ACA TAT GTT ACA TGC TCA AAG GAC TCT GAG GAG ACA CAC TTG CCC       1181
Lys Thr Tyr Val Thr Cys Ser Lys Asp Ser Glu Glu Thr His Leu Pro
330                 335                 340                 345

ACA GAG CTT TCA AAC ACA TAC ACC TTC CCC AAT CCC GCG CAC CCT CCA       1229
Thr Glu Leu Ser Asn Thr Tyr Thr Phe Pro Asn Pro Ala His Pro Pro
                350                 355                 360

GGA TCA CAG CCA GCG AAG CTA GGT TTA CTG TGC TCG CCA GAG AGA CTG       1277
Gly Ser Gln Pro Ala Lys Leu Gly Leu Leu Cys Ser Pro Glu Arg Leu
            365                 370                 375

CCT GAG GAG CTC TGC TAAGAGACGA TTGTCCACTC TTCCTCAAAA CTAGCACCAG T     1333
Pro Glu Glu Leu Cys
        380

CACACATACC TGGTCCTCTG AGTCACCGTC TGGGGTGTCC ACAGCACTAT AGATGCCTTT     1393

GTTCGGGCAC ACGCTGCTGA TCTTTCCTTC CTAAGGCCAC CAACTCTGAA AGTATCTGTT     1453

CCTTAAACTG TCCTCAGGCT CCCCTCTATG GAAAGCGGGG CTTGCTAAGG GACC           1507

(2) INFORMATION FOR SEQ ID NO:2:

(i) SEQUENCE CHARACTERISTICS:
        (A) LENGTH: 382 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Arg Ser Glu Pro Thr Asn Ala Ala Gly Asn Thr Thr Leu Gly Val
1               5                   10                  15
```

```
Thr Ser Val Leu Gln Ser Thr Ser Val Pro Ser Ser Glu Thr Cys His
            20                  25                  30

Val Ser Tyr Glu Glu Ser Arg Val Leu Val Val Tyr Ser Ala
            35                  40                  45

Val Cys Leu Leu Gly Leu Pro Ala Asn Cys Leu Thr Ala Trp Leu Thr
 50                  55                  60

Leu Leu Gln Val Leu Gln Arg Asn Val Leu Ala Val Tyr Leu Phe Cys
 65                  70                  75                  80

Leu Ser Leu Cys Glu Leu Leu Tyr Ile Ser Thr Val Pro Leu Trp Ile
                 85                  90                  95

Ile Tyr Ile Gln Asn Gln His Lys Trp Asn Leu Gly Pro Gln Ala Cys
                100                 105                 110

Lys Val Thr Ala Tyr Ile Phe Phe Cys Asn Ile Tyr Ile Ser Ile Leu
                115                 120                 125

Leu Leu Cys Cys Ile Ser Cys Asp Arg Tyr Met Ala Val Val Tyr Ala
130                 135                 140

Leu Glu Ser Arg Gly His Arg His Gln Arg Thr Ala Val Thr Ile Ser
145                 150                 155                 160

Ala Cys Val Ile Leu Leu Val Gly Leu Val Asn Tyr Pro Val Phe Asp
                165                 170                 175

Met Lys Val Glu Lys Ser Phe Cys Phe Glu Pro Leu Arg Met Asn Ser
                180                 185                 190

Lys Ile Ala Gly Tyr His Tyr Leu Arg Phe Thr Phe Gly Phe Ala Ile
                195                 200                 205

Pro Leu Gly Ile Leu Ala Phe Thr Asn His Gln Ile Phe Arg Ser Ile
210                 215                 220

Lys Leu Ser Asp Ser Leu Ser Ala Ala Gln Lys Asn Lys Val Lys Arg
225                 230                 235                 240

Ser Ala Ile Ala Val Val Thr Ile Phe Leu Val Cys Phe Ala Pro Tyr
                245                 250                 255

His Val Val Leu Leu Val Lys Ala Ala Ser Phe Ser Phe Tyr Gln Gly
                260                 265                 270

Asp Met Asp Ala Val Cys Ala Phe Glu Ser Arg Leu Tyr Thr Val Ser
                275                 280                 285

Met Val Phe Leu Cys Leu Ser Thr Val Asn Ser Val Ala Asp Pro Ile
                290                 295                 300

Ile Tyr Val Leu Gly Thr Asp His Ser Arg Gln Glu Val Ser Arg Ile
305                 310                 315                 320

His Thr Gly Trp Lys Lys Trp Ser Thr Lys Thr Tyr Val Thr Cys Ser
                325                 330                 335

Lys Asp Ser Glu Glu Thr His Leu Pro Thr Glu Leu Ser Asn Thr Tyr
                340                 345                 350

Thr Phe Pro Asn Pro Ala His Pro Pro Gly Ser Gln Pro Ala Lys Leu
                355                 360                 365

Gly Leu Leu Cys Ser Pro Glu Arg Leu Pro Glu Glu Leu Cys
    370                 375                 380

(2) INFORMATION FOR SEQ ID NO:3:

(i) SEQUENCE CHARACTERISTICS:
        (A) LENGTH: 2938 base pairs
        (B) TYPE: nucleic acid
        (C) STRANDEDNESS: single
        (D) TOPOLOGY: linear (ii) MOLECULE TYPE: Other
```

(ix) FEATURE:
    (A) NAME/KEY: Coding Sequence
    (B) LOCATION: 901...2040
    (D) OTHER INFORMATION:

(xi) SEQUENCE DESCRIPTION: SEQ ID NO:3:

```
GGGAGGGGTG CNANGCTAGC CACGCAGGCG GGGCCCTGGG TCATTTTAAN CTCTCAGAGT      60

GAACGTCTTG ATAGGACCGA CAANACNCAT NACNTGTACT TAGATAGCTT ATCTTANANC     120

CACNCTGANA TTGGAACCCG CAAAATATGC CNGGGAGGAA GGTGAGCAAG GGACACGACA     180

CTCACCCGGA TAAACCCAAC AAGCGCAGCG AGGCTGTGGG GAAACCGGAN CCCTGCACAC     240

CGCCGGGGGA AGGTGGGCCN CCGCCACCAC CGTGGAAGAA CAGCGCGGAN GCACCCCACG     300

AGATGAGACG GAACTGCCGT GAGATCCAGC AATNCCNACT GTGGGTCTGA CCCAGGATAN     360

CGGAAAGCAG GGACGTGAAC AGCCCTCCTC ATGTTCTTGA CACCGTCATT CTCAGCAGCT     420

CAGCTAAGGC ACAGAGGCAG CCGAGCGTCT GTCAGCAGAG TCGTGGCTGA GCAGAACACG     480

CCACACGCCA CACGCCACAC GCCACACGTG CAGGATTGCT CAAGATGGAA GGGCACAGTG     540

GAATATATAT ATATATTTAT ATTTTTGGCG AGACCCTGGA GGACACACTG AATACAATGG     600

AATACCATCC CGCCTTTGAA AGGAAGGGAA ATCCTGGCAC ACGCTGCAAC AGGAGGGAGC     660

TTGAGGACAC TGTGGTGAGT GGAGCACGTG AGACACGGAA GGACACACGC TGAAGACACG     720

CAGAGATGCC CACCCACGTG GGGAGGTGAC AGGGGAGCCC AGCGCACAGA GACAAAGTGG     780

AATGGAGGCC TGGGGGCTGG GAGCAAATGC GGAGCGAGTG CTTCCTGGGG CAGAGTCTCC     840

GTTTGGGAAG ATGAGAAGGT TCTGCCGACG GATGCTGGCG ATGGTTGCAG AAGAATGTGA     900
```

```
ATG TGC CCA ATG CTA CTG AAA AAC GGT TAC AAT GGA AAC GCC ACC CCA       948
Met Cys Pro Met Leu Leu Lys Asn Gly Tyr Asn Gly Asn Ala Thr Pro
 1               5                  10                  15

GTG ACC ACC ACT GCC CCG TGG GCC TCC CTG GGC CTC TCC GCC AAG ACC       996
Val Thr Thr Thr Ala Pro Trp Ala Ser Leu Gly Leu Ser Ala Lys Thr
                20                  25                  30

TGC AAC AAC GTG TCC TTC GAA GAG AGC AGG ATA GTC CTG GTC GTG GTG      1044
Cys Asn Asn Val Ser Phe Glu Glu Ser Arg Ile Val Leu Val Val Val
            35                  40                  45

TAC AGC GCG GTG TGC ACG CTG GGG GTG CCG GCC AAC TGC CTG ACT GCG      1092
Tyr Ser Ala Val Cys Thr Leu Gly Val Pro Ala Asn Cys Leu Thr Ala
 50                  55                  60

TGG CTG GCG CTG CTG CAG GTA CTG CAG GGC AAC GTG CTG GCC GTC TAC      1140
Trp Leu Ala Leu Leu Gln Val Leu Gln Gly Asn Val Leu Ala Val Tyr
 65                  70                  75                  80

CTG CTC TGC CTG GCA CTC TGC GAG CTG CTG TAC ACA GGC ACG CTG CCA      1188
Leu Leu Cys Leu Ala Leu Cys Glu Leu Leu Tyr Thr Gly Thr Leu Pro
                85                  90                  95

CTC TGG GTC ATC TAT ATC CGC AAC CAG CAC CGC TGG ACC CTA GGC CTG      1236
Leu Trp Val Ile Tyr Ile Arg Asn Gln His Arg Trp Thr Leu Gly Leu
                100                 105                 110

CTG GCC TGC AAG GTG ACC GCC TAC ATC TTC TTC TGC AAC ATC TAC GTC      1284
Leu Ala Cys Lys Val Thr Ala Tyr Ile Phe Phe Cys Asn Ile Tyr Val
            115                 120                 125

AGC ATC CTC TTC CTG TGC TGC ATC TCC TGC GAC CGC TTC GTG GCC GTG      1332
Ser Ile Leu Phe Leu Cys Cys Ile Ser Cys Asp Arg Phe Val Ala Val
130                 135                 140

GTG TAC GCG CTG GAG AGT CGG GGC CGC CGC CGC CGG AGG ACC GCC ATC      1380
Val Tyr Ala Leu Glu Ser Arg Gly Arg Arg Arg Arg Thr Ala Ile
145                 150                 155                 160

CTC ATC TCC GCC TGC ATC TTC ATC CTC GTC GGG ATC GTT CAC TAC CCG      1428
```

```
                                                          -continued

Leu Ile Ser Ala Cys Ile Phe Ile Leu Val Gly Ile Val His Tyr Pro
                165                 170                 175

GTG TTC CAG ACG GAA GAC AAG GAG ACC TGC TTT GAC ATG CTG CAG ATG      1476
Val Phe Gln Thr Glu Asp Lys Glu Thr Cys Phe Asp Met Leu Gln Met
            180                 185                 190

GAC AGC AGG ATT GCC GGG TAC TAC TAC GCC AGG TTC ACC GTT GGC TTT      1524
Asp Ser Arg Ile Ala Gly Tyr Tyr Tyr Ala Arg Phe Thr Val Gly Phe
                195                 200                 205

GCC ATC CCT CTC TCC ATC ATC GCC TTC ACC AAC CAC CGG ATT TTC AGG      1572
Ala Ile Pro Leu Ser Ile Ile Ala Phe Thr Asn His Arg Ile Phe Arg
            210                 215                 220

AGC ATC AAG CAG AGC ATG GGC TTA AGC GCT GCC CAG AAG GCC AAG GTG      1620
Ser Ile Lys Gln Ser Met Gly Leu Ser Ala Ala Gln Lys Ala Lys Val
225                 230                 235                 240

AAG CAC TCG GCC ATC GCG GTG GTT GTC ATC TTC CTA GTC TGC TTC GCC      1668
Lys His Ser Ala Ile Ala Val Val Val Ile Phe Leu Val Cys Phe Ala
                245                 250                 255

CCG TAC CAC CTG GTT CTC CTC GTC AAA GCC GCT GCC TTT TCC TAC TAC      1716
Pro Tyr His Leu Val Leu Leu Val Lys Ala Ala Ala Phe Ser Tyr Tyr
            260                 265                 270

AGA GGA GAC AGG AAC GCC ATG TGC GGC TTG GAG GAA AGG CTG TAC ACA      1764
Arg Gly Asp Arg Asn Ala Met Cys Gly Leu Glu Glu Arg Leu Tyr Thr
                275                 280                 285

GCC TCT GTG GTG TTT CTG TGC CTG TCC ACG GTG AAC GGC GTG GCT GAC      1812
Ala Ser Val Val Phe Leu Cys Leu Ser Thr Val Asn Gly Val Ala Asp
            290                 295                 300

CCC ATT ATC TAC GTG CTG GCC ACG GAC CAT TCC CGC CAA GAA GTG TCC      1860
Pro Ile Ile Tyr Val Leu Ala Thr Asp His Ser Arg Gln Glu Val Ser
305                 310                 315                 320

AGA ATC CAT AAG GGG TGG AAA GAG TGG TCC ATG AAG ACA GAC GTC ACC      1908
Arg Ile His Lys Gly Trp Lys Glu Trp Ser Met Lys Thr Asp Val Thr
                325                 330                 335

AGG CTC ACC CAC AGC AGG GAC ACC GAG GAG CTG CAG TCG CCC GTG GCC      1956
Arg Leu Thr His Ser Arg Asp Thr Glu Glu Leu Gln Ser Pro Val Ala
            340                 345                 350

CTT GCA GAC CAC TAC ACC TTC TCC AGG CCC GTG CAC CCA CCA GGG TCA      2004
Leu Ala Asp His Tyr Thr Phe Ser Arg Pro Val His Pro Pro Gly Ser
                355                 360                 365

CCA TGC CCT GCA AAG AGG CTG ATT GAG GAG TCC TGC TGAGCCCACT GTGTGG    2056
Pro Cys Pro Ala Lys Arg Leu Ile Glu Glu Ser Cys
            370                 375                 380

CAGGGGGATG GCAGGTTGGG GGTCCTGGGG CCAGCAATGT GGTTCCTGTG CACTGAGCCC    2116

ACCAGCCACA GTGCCCATGT CCCCTCTGGA AGACAAACTA CCAATTTCTC GTTCCTGAAG    2176

CCACTCCCTC CGTGACCACT GGCCCCANGC TTTCCCACAT GGAAGGTGGC TGCATGCCAA    2236

GGGGAAGAAC GACACCTCCA GGCTTCCGGG AGCCCANANA NCATGTGGCA NGCAGTGGGG    2296

CCTCTTCATC ATCANCCTGC CTGGCTGGCT CCCTTGGCTG TGGGCANGTA CACCCCTGCT    2356

GGCANAAGTA CCTGGTGGCT GCCCTGTTCG CATCANTGGC GATNACTTTA TTTGCGGAGC    2416

ATTTCTGCAA NCGTTGCCTG GATNCGGTGG TGCATTGTGG GCCCTCTGGG CTCCTGCCTC    2476

AAAATGTCAG TGANCACCAT GCTGGAAGTC ACCATCACTG TGGCANCGCC CANGAAGGCA    2536

TANGGCACCT ACCACCTCCA ANGGGGCANG CGCCCTCATC TGGGGTTGGG TCTNTTGCTG    2596

AACTGGGAAG GCCTCTANGG GAACCCTGGG GCANGGTGGC CAACTGCTNG CTCCCANAAA    2656

CCAACCCAAG GCGTCTCAAC GGGGGAACCC CAAATGTTCN CGCCCCANAA AAAACAATTT    2716

TNGGAAGGAN AAGTTNTTAA ACACCCCNCC NCCANAAGCC AAGGGGTTCC CAGGAAATTC    2776
```

```
CCCACCGGCA TCCTCCGGGG AAAANACTCG GTNAANGGGT CCCTTACAAG GGTTGGGGGT      2836

TCCCCNCCCC TAACCCCCNT TAATTGAAGG GGGGGAAATT CAACCCTTTT GGCCTCCTTT      2896

TTTTTTGCGG NAAAAAAAAC AACNTCCCCT GCANCCCCCG GN                         2938
```

(2) INFORMATION FOR SEQ ID NO:4:

(i) SEQUENCE CHARACTERISTICS:
        (A) LENGTH: 380 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

```
Met Cys Pro Met Leu Leu Lys Asn Gly Tyr Asn Gly Asn Ala Thr Pro
 1               5                  10                  15

Val Thr Thr Thr Ala Pro Trp Ala Ser Leu Gly Leu Ser Ala Lys Thr
                20                  25                  30

Cys Asn Val Ser Phe Glu Glu Ser Arg Ile Val Leu Val Val Val
            35                  40                  45

Tyr Ser Ala Val Cys Thr Leu Gly Val Pro Ala Asn Cys Leu Thr Ala
50                  55                  60

Trp Leu Ala Leu Leu Gln Val Leu Gln Gly Asn Val Leu Ala Val Tyr
65                  70                  75                  80

Leu Leu Cys Leu Ala Leu Cys Glu Leu Leu Tyr Thr Gly Thr Leu Pro
                85                  90                  95

Leu Trp Val Ile Tyr Ile Arg Asn Gln His Arg Trp Thr Leu Gly Leu
                100                 105                 110

Leu Ala Cys Lys Val Thr Ala Tyr Ile Phe Phe Cys Asn Ile Tyr Val
                115                 120                 125

Ser Ile Leu Phe Leu Cys Cys Ile Ser Cys Asp Arg Phe Val Ala Val
130                 135                 140

Val Tyr Ala Leu Glu Ser Arg Gly Arg Arg Arg Arg Thr Ala Ile
145                 150                 155                 160

Leu Ile Ser Ala Cys Ile Phe Ile Leu Val Gly Ile Val His Tyr Pro
                165                 170                 175

Val Phe Gln Thr Glu Asp Lys Glu Thr Cys Phe Asp Met Leu Gln Met
                180                 185                 190

Asp Ser Arg Ile Ala Gly Tyr Tyr Ala Arg Phe Thr Val Gly Phe
                195                 200                 205

Ala Ile Pro Leu Ser Ile Ile Ala Phe Thr Asn His Arg Ile Phe Arg
210                 215                 220

Ser Ile Lys Gln Ser Met Gly Leu Ser Ala Ala Gln Lys Ala Lys Val
225                 230                 235                 240

Lys His Ser Ala Ile Ala Val Val Ile Phe Leu Val Cys Phe Ala
                245                 250                 255

Pro Tyr His Leu Val Leu Val Lys Ala Ala Ala Phe Ser Tyr Tyr
                260                 265                 270

Arg Gly Asp Arg Asn Ala Met Cys Gly Leu Glu Glu Arg Leu Tyr Thr
                275                 280                 285

Ala Ser Val Val Phe Leu Cys Leu Ser Thr Val Asn Gly Val Ala Asp
290                 295                 300

Pro Ile Ile Tyr Val Leu Ala Thr Asp His Ser Arg Gln Glu Val Ser
```

```
             305                 310                 315                 320
Arg Ile His Lys Gly Trp Lys Glu Trp Ser Met Lys Thr Asp Val Thr
                    325                 330                 335

Arg Leu Thr His Ser Arg Asp Thr Glu Glu Leu Gln Ser Pro Val Ala
                340                 345                 350

Leu Ala Asp His Tyr Thr Phe Ser Arg Pro Val His Pro Pro Gly Ser
                355                 360                 365

Pro Cys Pro Ala Lys Arg Leu Ile Glu Glu Ser Cys
                370                 375                 380
```

(2) INFORMATION FOR SEQ ID NO:5:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Lys Asp Ser Glu Glu Thr His Leu Pro Thr Glu Leu Ser
 1               5                  10
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:6:

AGCACTCTCC AGCCTCTCAC CGCA                                    24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:7:

ACCGACGTCG ACTATCCATG AACA                                    24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:8:

AGGCAACTGT GCTATCCGAG GGAA                                    24

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:9:

```
GATCTGCGGT GA                                                                   12

(2) INFORMATION FOR SEQ ID NO:10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:10:

GATCTGTTCA TG                                                                   12

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:11:

GATCTTCCCT CG                                                                   12

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:12:

CAGGACTGGC TTGGGTCATT                                                           20

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:13:

GTCCACAGAA CTCACATAGG A                                                         21

(2) INFORMATION FOR SEQ ID NO:14:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:14:

CGCGGATCCG AATTCGGTAC CGGTGACTCA GAGGACCAG                                      39

(2) INFORMATION FOR SEQ ID NO:15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:15:
```

```
CGGAATTCTC GAGTCAGGAC TGGCTTGGGT CATT                           34
```

(2) INFORMATION FOR SEQ ID NO:16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:16:

```
ATAGTTTAGC GGCCGCGCAG AGCTCCTCAG GCAGT                          35
```

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:17:

```
CAAGAAGTGT CCAGAATCCA                                           20
```

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:18:

```
GGTGACAGCA GTCCTCTGGT                                           20
```

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:19:

```
TAGCGGTCGC AGGAAATGCA G                                         21
```

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:20:

```
TGATTGGTGA ACGCCAGG                                             18
```

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:21:

```
GCTTTGAGCC CCTGAGGATG AA                                        22
```

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:22:

GTAATACGAC TCACTATAGG GC                                     22

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:23:

GTCGGATCCA TGAGATCAGA ACCTACCAAT                          30

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:24:

GTCGAATTCT CACAGGACCA CTCTGCTCTC                          30

(2) INFORMATION FOR SEQ ID NO:25:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:25:

CAGGAAACAG CTATGAC                                               17

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:26:

CUACUACUAC UAGGCCACGC GTCGACTAGT ACGGGGGGGG GG              42

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:27:

GCCGAATTCT CAAACTCCGG C                                    21

(2) INFORMATION FOR SEQ ID NO:28:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:28:

```
CCGGAATTCG GCCACCATGG ACTACAAGGA CGACGATGAC AAGAGATCAG AACCTACCAA      60

TGCA                                                                  64
```

(2) INFORMATION FOR SEQ ID NO:29:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:29:

```
CCGGAATTCC TAGAGGCCAC CATGAGATCA GAACCTACCA AT                        42
```

(2) INFORMATION FOR SEQ ID NO:30:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:30:

```
CGCTCGAGTG GGAGCAAATG CGGAGCGAG                                       29
```

(2) INFORMATION FOR SEQ ID NO:31:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:31:

```
TTAGCGGCCG CTCAGCAGGA CTCCTCAATC AG                                   32
```

(2) INFORMATION FOR SEQ ID NO:32:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:32:

```
TTAGCGGCCG CGCAGGACTC CTCAATCAGC CTC                                  33
```

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:33:

```
CAAGAAGTGT CCAGAATCCA                                                 20
```

(2) INFORMATION FOR SEQ ID NO:34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:34:

ACCAGCCACA GTGCCCATG                                            19

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:35:

TGCCACTCTG GGTCATCTAT                                          20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:36:

CGGTGGTTGT CATCTTCCTA                                          20

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:37:

GTAATACGAC TCACTATAGG GC                                      22

(2) INFORMATION FOR SEQ ID NO:38:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:38:

CAGGAAACAG CTATGAC                                                17

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:39:

ACCACAGTCC ATGCCATCAC                                          20

(2) INFORMATION FOR SEQ ID NO:40:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:40:

TCCACCACCC TGTTGCTGTA      20